United States Patent
Schimperna et al.

(10) Patent No.: US 11,208,406 B2
(45) Date of Patent: Dec. 28, 2021

(54) DISUBSTITUTED DIARYLOXYBENZOHETERODIAZOLE COMPOUNDS

(71) Applicant: Eni S.p.A., Rome (IT)

(72) Inventors: Giuliana Schimperna, Novara (IT); Antonio Alfonso Proto, Novara (IT)

(73) Assignee: Eni S.P.A., Rome (IT)

( * ) Notice: Subject to any disclaimer, the term of this patent is extended or adjusted under 35 U.S.C. 154(b) by 674 days.

(21) Appl. No.: 15/774,212

(22) PCT Filed: Nov. 11, 2016

(86) PCT No.: PCT/IB2016/056793
§ 371 (c)(1),
(2) Date: May 7, 2018

(87) PCT Pub. No.: WO2017/081645
PCT Pub. Date: May 18, 2017

(65) Prior Publication Data
US 2018/0327400 A1 Nov. 15, 2018

(30) Foreign Application Priority Data

Nov. 13, 2015 (IT) .................. 102015000072291

(51) Int. Cl.
*C07D 417/14* (2006.01)
*C09K 11/06* (2006.01)
(Continued)

(52) U.S. Cl.
CPC ............ *C07D 417/14* (2013.01); *C09K 11/06* (2013.01); *H01L 31/055* (2013.01); *C09K 11/02* (2013.01);
(Continued)

(58) Field of Classification Search
CPC .................. C07D 417/14; C09K 11/06; C09K 2211/1051; C09K 2211/1092;
(Continued)

(56) References Cited

U.S. PATENT DOCUMENTS

| 2006/0052612 A1* | 3/2006 | Stossel | C07D 417/14 548/126 |
| 2008/0093985 A1* | 4/2008 | Morishita | C07C 211/54 313/504 |
| 2011/0003250 A1* | 1/2011 | Amara | C07C 69/76 430/271.1 |

FOREIGN PATENT DOCUMENTS

| EP | 2730600 A1 * | 5/2014 | ......... H01L 51/0036 |
| IT | MI2014A001663 A | 9/2014 | |

(Continued)

OTHER PUBLICATIONS

Masaru Yanagisawa "Synthesis of phthalocyanines with two carboxylic acid groups and their utilization in solar cells based on nanostructured TiO2" J. Porphyrins Phthalocyanines 2004; 8: 1228-1235 (Year: 2004).*

(Continued)

*Primary Examiner* — Michael Y Sun
(74) *Attorney, Agent, or Firm* — Praedcere Law

(57) ABSTRACT

Disubstituted diaryloxybenzoheterodiazole compound having general formula (I) or (II) and luminescent solar concentrator (LSC) including the same:

(Continued)

-continued (II)

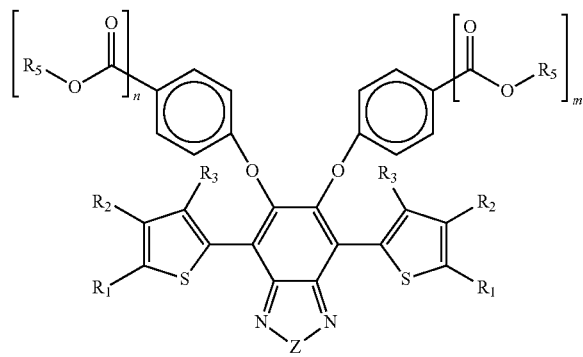

wherein:
- Z represents a sulfur atom, an oxygen atom, a selenium atom; or an $NR_6$ group wherein $R_6$ is selected from linear or branched $C_1$-$C_{20}$ alkyl groups, or from optionally substituted aryl groups;
- $R_1$, $R_2$ and $R_3$, identical or different, represent a hydrogen atom; or are selected from linear or branched $C_1$-$C_{20}$ alkyl groups optionally containing heteroatoms, optionally substituted cycloalkyl groups, optionally substituted aryl groups, optionally substituted linear or branched $C_1$-$C_{20}$ alkoxy groups, optionally substituted phenoxy groups, or a cyano group;
- or $R_1$ and $R_2$, may optionally be bound together to form, together with the carbon atoms to which they are bound, a saturated, unsaturated or aromatic, cyclic or polycyclic system containing from 3 to 14 carbon atoms, optionally containing one or more heteroatoms;
- or $R_2$ and $R_3$, may optionally be bound together so as to form, together with the carbon atoms to which they are bound, a saturated, unsaturated or aromatic, cyclic or polycyclic system containing from 3 to 14 carbon atoms, optionally containing one or more heteroatoms;
- $R_4$, identical or different, represent a hydrogen atom; or are selected from linear or branched $C_1$-$C_{20}$ alkyl groups;
- $R_5$, identical or different, are selected from linear or branched $C_1$-$C_{20}$ alkyl groups, optionally containing heteroatoms, or optionally substituted cycloalkyl groups;
- n and m, identical or different, are 0 or 1, provided that at least one of n and m is 1.

8 Claims, 2 Drawing Sheets

(51) Int. Cl.

| | |
|---|---|
| *H01L 31/055* | (2014.01) |
| *H01L 51/00* | (2006.01) |
| *H01L 51/44* | (2006.01) |
| *C09K 11/02* | (2006.01) |
| *H01L 31/0232* | (2014.01) |
| *H01L 27/30* | (2006.01) |
| *H01L 27/146* | (2006.01) |
| *H01L 51/42* | (2006.01) |
| *H02S 40/22* | (2014.01) |

(52) U.S. Cl.
CPC ............ *C09K 2211/1007* (2013.01); *C09K 2211/1011* (2013.01); *C09K 2211/1051* (2013.01); *C09K 2211/1092* (2013.01); *H01L 27/14663* (2013.01); *H01L 27/301* (2013.01); *H01L 31/02322* (2013.01); *H01L 51/004* (2013.01); *H01L 51/0058* (2013.01); *H01L 51/0068* (2013.01); *H01L 51/0071* (2013.01); *H01L 51/4206* (2013.01); *H01L 51/447* (2013.01); *H02S 40/22* (2014.12); *Y02E 10/52* (2013.01); *Y02E 10/549* (2013.01)

(58) Field of Classification Search
CPC ............ C09K 11/02; C09K 2211/1007; C09K 2211/1011; H01L 31/055; H01L 51/0071; H01L 51/0058; H01L 51/4206; H01L 51/0068; H01L 51/447; H01L 27/301; H01L 51/004; H01L 31/02322; H01L 27/14663; Y02E 10/52; Y02E 10/549; H02S 40/22
See application file for complete search history.

(56) References Cited

FOREIGN PATENT DOCUMENTS

| WO | WO 2011/048458 A1 | 4/2011 |
| WO | WO2011048458 A1 | 4/2011 |
| WO | WO 2012/007834 A1 | 1/2012 |
| WO | WO2012007834 A1 | 1/2012 |
| WO | WO 2013/005177 A2 | 1/2013 |
| WO | WO 2014/108873 A1 | 7/2014 |
| WO | WO 2015/049631 A1 | 4/2015 |
| WO | WO2015049631 A1 | 4/2015 |

OTHER PUBLICATIONS

International Search Report & Written opinion for PCT/IB2016/056793, dated Feb. 3, 2017, 10 pages.
Wang, L.-Y. et al., in "Macromo/ecules" (2010), vol. 43, p. 1277-1288.
Kularatne, R. S. et al., in "Journal of Materials Chemistry A" (2013), vol. 1 (48), p. 15535-15543.
Wang N. et al., in"Journal of the American Chemical Society" (2013), vol. 135(45), p. 17060-17068.
Zhou, H. et al., in "Angewandte Chemie International Edition" (2011), vol. 50( 13), p. 2995-2998.
Office action issued by the Indian Patent Office for Indian patent application 201817017142 dated May 26, 2020, 7 pages. Translation in English included in text.
4237/CHENP/2012 published May 14, 2012, claims & description (corresponds to WO2011048458A1, listed above).
1387/DELNP/2013, published Feb. 14, 2013, claims & description (corresponds to WO2012007834A1, listed above).
Fushun Lianga et al, Donor-acceptor conjugatesfunctionalized-zinc phthalocyanine:Towards broad absorption and application in organic solar cells, Solar Energy Materials and Solar Cells, vol. 94, Issue 10, Oct. 2010, pp. 1803-1808.
Marappah Velusamy et al, "Organic Dyes Incorporating Low-Band-Gap Chromophores for Dye-Sensitized Solar Cells", Organic Letters, 7, 10, 1899-1902, Publication Date: Apr. 20, 2005.
Nastaran Irani et al, "Esterification of 3,5-dinitrobenzoic acid with 2-hydroxyethyl methacrylate polymers", Journal of Chemical and Pharmaceutical Research, 2015, 7(10):677-692.
Yi Zhanga et al, "The coupling reactions of aryl halides and phenols catalyzed by palladium and MOP-type ligands", Tetrahedron, vol. 71, issue 30, Jul. 29, 2015, pp. 4927-4932.

* cited by examiner

DISUBSTITUTED DIARYLOXYBENZOHETERODIAZOLE COMPOUNDS

The present invention relates to a disubstituted diaryloxybenzoheterodiazole compound. More particularly the present invention relates to a diaryloxybenzoheterodiazole compound disubstituted with thiophene groups having the general formula (I) or (II) shown below.

The present invention also relates to processes for preparing said diaryloxybenzoheterodiazole compound disubstituted with thiophene groups.

Said disubstituted diaryloxybenzoheterodiazole compound having general formula (I), as such or after (co)polymerization, and said disubstituted diaryloxybenzoheterodiazole compound having general formula (II), as such, may advantageously be used as spectrum converters in luminescent solar concentrators (LSCs), which are in turn capable improving the performance of photovoltaic devices (or solar devices) selected, for example, from photovoltaic cells (or solar cells), photovoltaic modules (or solar modules), on both rigid and flexible supports.

The present invention also relates to a luminescent solar concentrator (LSC) including at least one diaryloxybenzoheterodiazole compound disubstituted with thiophene groups having general formula (I) or (II), and to a photovoltaic device (or solar device) comprising said luminescent solar concentrator (LSC).

In the state of the art, one of the main limitations on the utilisation of energy from solar radiation is represented by the capacity of photovoltaic devices (or solar devices) to absorb optimally only radiation having a wavelength falling within a narrow spectral range.

In contrast with the spectral range of solar radiation, which extends from wavelengths of approximately 300 nm to wavelengths of approximately 2500 nm, photovoltaic cells (or solar cells) based for example on crystalline silicon have an optimum absorption zone (effective spectrum) in the range 900 nm-1100 nm, while polymer photovoltaic cells (or solar cells) are likely to become damaged if exposed to radiation having a wavelength of below approximately 500 nm, because of induced photodegradation phenomena which become significant below that limit. Typically, the efficiency of the photovoltaic devices (or solar devices) in the state of the art is a maximum in the spectral region ranging from 570 nm to 680 nm (yellow-orange).

The inconveniences mentioned above give rise to limited external quantum efficiency (EQE) in photovoltaic devices (or solar devices), defined as the ratio between the number of electron-hole pairs generated in the semiconductor material of the photovoltaic devices (or solar devices) and the number of photons incident upon said photovoltaic devices (or solar devices).

In order to improve the external quantum efficiency (EQE) of photovoltaic devices (or solar devices), means have been developed which selectively absorb incident radiation having wavelengths outside the effective spectrum of said photovoltaic devices (or solar devices) when placed between the source of light radiation (the sun) and the photovoltaic devices (or solar devices), emitting the absorbed energy in the form of photons of wavelength lying within the effective spectrum. These means have been called luminescent solar concentrators (LSCs). When the energy of the photons re-emitted from the luminescent solar concentrators (LSCs) is higher than that of the incident photons, the process of photoluminescence, comprising the absorption of solar radiation and the subsequent re-emission of photons at a shorter wavelength, is also referred to as "up-conversion". On the contrary, when the energy of the photons emitted from the luminescent solar concentrators (LSCs) is below that of the incident photons, the process of photoluminescence is defined as a "down-conversion" (or "down-shifting") process. Generally, said luminescent solar concentrators (LSCs) comprise large sheets of a material transparent to solar radiation (for example, polymer or inorganic glasses), within which fluorescent compounds acting as spectrum converters are dispersed or chemically bound to said material. Through the effect of the optical phenomenon of total reflection, the radiation emitted by the fluorescent compounds is "guided" towards the thin edges of the sheet where it is concentrated on photovoltaic cells (or solar cells) located there. In this way large surface areas of low-cost material (the photoluminescent sheets) may be used to concentrate the light on small surface areas of materials of high cost [photovoltaic cells (or solar cells)].

The fluorescent compounds may be deposited on the glass substrate in the form of thin films or, as in case of polymer materials, they may be dispersed within the polymer matrix. Alternatively the polymer matrix may be directly functionalised with fluorescent chromophore groups.

Ideally, fluorescent compounds must have the following properties in order to be used in spectrum converters:
  high quantum efficiency of luminescence ($\phi$) [($\phi$) is defined as in equation (1) shown below as the ratio between the number of photons emitted and the number of photons absorbed by a luminescent molecule per unit time, and has a maximum value of 1]:

$$(\phi) = \text{number of photons emitted/number of photons absorbed} \qquad (1);$$

a wide absorption band in the spectral region wherein the photovoltaic device (or solar device) has very little efficiency;
  a high absorption coefficient;
  a narrow emission band in the spectral region wherein the photovoltaic device (or solar device) is more efficient;
  well-separated absorption and emission bands to avoid or minimise self-absorption phenomena.

It is known that some benzothiadiazole compounds, in particular 4,7-di-(thien-2'-yl)-2,1,3-benzothiadiazole (DTB), are fluorescent compounds that may be used in the construction of luminescent solar concentrators (LSCs). Compounds of this type have been described in International Patent Application WO 2011/048458 in the name of the Applicant. 4,7-di-(thien-2'-yl)-2,1,3-benzothiadiazole (DTB) is characterised by emission centred around 579 nm, a value corresponding to an energy well above the minimum operating threshold of photovoltaic cells (or solar cells), a threshold which, for example, corresponds to a wavelength of approximately 1100 nm in the most commonly used silicon-based photovoltaic cells (or solar cells). In addition to this their light radiation absorption is intense and extends over a relatively wide range of wavelengths, indicatively included between 550 nm (the wavelength of green radiation) and the ultraviolet. Finally 4,7-di-(thien-2'-yl)-2,1,3-benzothiadiazole (DTB) has a Stokes shift of 134 nm in dichloromethane solution, well above that of most of the commercial products hitherto offered for use in luminescent solar concentrators (LSCs).

For these reasons, the use of 4,7-di-(thien-2'-yl)-2,1,3-benzothiadiazole (DTB) has made it possible to manufacture luminescent solar concentrators (LSCs) of excellent quality. However, although 4,7-di-(thien-2'-yl)-2,1,3-benzothiadiazole (DTB) absorbs a significant part of the solar spectrum, it shows poor absorption in its longer wavelength regions corresponding to yellow and red radiation, which may therefore not be converted into others more effectively utilised by photovoltaic cells (or solar cells).

Italian Patent Application MI2014A001663 in the name of the Applicant describes a disubstituted diaryloxybenzoheterodiazole compound having general formula (I):

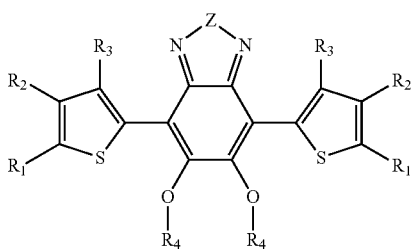

wherein:
- Z represents a sulfur atom, an oxygen atom, a selenium atom; or an NRs group wherein $R_5$ is selected from linear or branched $C_1$-$C_{20}$, preferably $C_1$-$C_8$, alkyl groups, or optionally substituted aryl groups;
- $R_1$, $R_2$ and $R_3$, identical or different, represent a hydrogen atom; or are selected from linear or branched $C_1$-$C_{20}$, preferably $C_1$-$C_8$, alkyl groups optionally containing heteroatoms, optionally substituted cycloalkyl groups, optionally substituted aryl groups, optionally substituted linear or branched $C_1$-$C_{20}$, preferably $C_1$-$C_8$, alkoxy groups, optionally substituted phenoxy groups, or a cyano group;
- or $R_1$ and $R_2$, may optionally be bound together so as to form, together with the carbon atoms to which they are bound, a saturated, unsaturated or aromatic, cyclic or polycyclic system containing from 3 to 14 carbon atoms, preferably from 4 to 6 carbon atoms, optionally containing one or more heteroatoms such as, for example, oxygen, sulfur, nitrogen, silicon, phosphorus, selenium;
- or $R_2$ and $R_3$, may optionally be bound together so as to form, together with the carbon atoms to which they are bound, a saturated, unsaturated or aromatic, cyclic or polycyclic system containing from 3 to 14 carbon atoms, preferably from 4 to 6 carbon atoms, containing one or more heteroatoms such as, for example, oxygen, sulfur, nitrogen, silicon, phosphorus, selenium;
- $R_4$, identical or different, are selected from optionally substituted aryl groups.

The aforesaid diaryloxybenzoheterodiazole compound disubstituted with thiophene groups has been said to be advantageously capable of being used as a spectrum converter in luminescent solar concentrators (LSCs), which are in turn capable of improving the performance of photovoltaic devices (or solar devices) selected, for example, from photovoltaic cells (or solar cells), photovoltaic modules (or solar modules), on both rigid and flexible supports.

The investigation of new compounds capable of providing performance similar to or even an improvement upon such performance, in particular in terms of the power generated by photovoltaic devices (or solar devices) wherein they are used, is however of great interest.

The Applicant has therefore set itself the problem of finding disubstituted diaryloxybenzoheterodiazole compounds capable of providing performance comparable to or even better than known benzothiadiazole compounds, in particular in terms of the power generated by the photovoltaic devices wherein they are used.

The Applicant has now found disubstituted diaryloxybenzoheterodiazole compounds having specific general formulae [i.e. having general formula (I) or (II) shown below], which may advantageously be used as such, or, in the case of compounds having general formula (I), also after (co) polymerization, as spectrum converters in the construction of luminescent solar concentrators (LSCs). Said luminescent solar concentrators (LSCs) may in turn be advantageously used together, for example, with photovoltaic cells (or solar cells), in the construction of photovoltaic devices (or solar devices). Said disubstituted diaryloxybenzoheterodiazole compounds are able to provide performance comparable to or even better than known benzothiadiazole compounds, in particular in terms of the power generated by the photovoltaic devices wherein they are used.

One object of the present invention is therefore a disubstituted diaryloxybenzoheterodiazole compound having general formula (I) or (II):

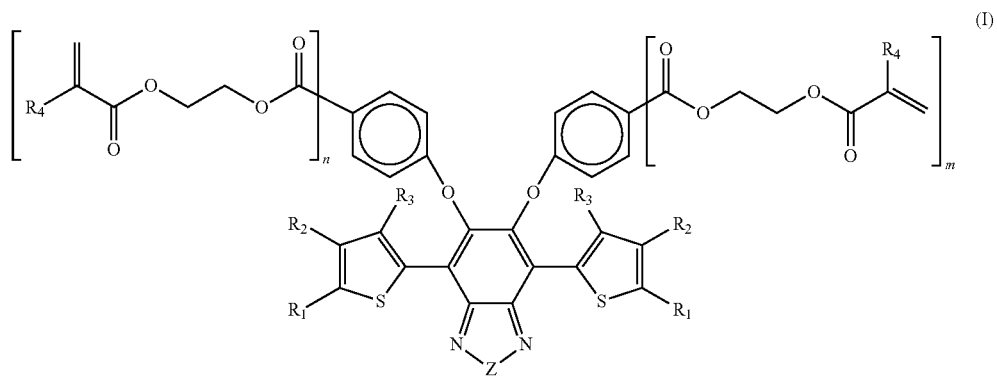

(II)

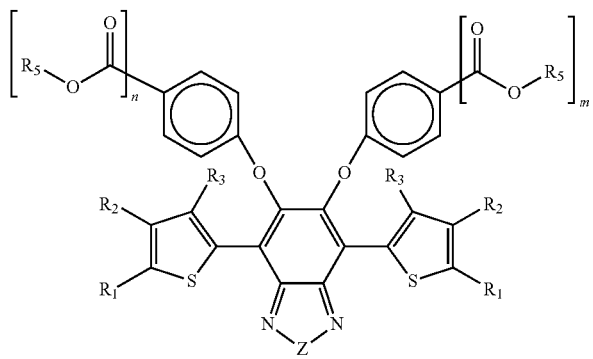

wherein:
Z represents a sulfur atom, an oxygen atom, a selenium atom; or an NRs group wherein $R_6$ is selected from linear or branched $C_1$-$C_{20}$, preferably $C_1$-$C_8$, alkyl groups, or from optionally substituted aryl groups;

$R_1$, $R_2$ and $R_3$, identical or different, represent a hydrogen atom; or are selected from linear or branched $C_1$-$C_{20}$, preferably $C_1$-$C_8$, alkyl groups optionally containing heteroatoms, optionally substituted cycloalkyl groups, optionally substituted aryl groups, optionally substituted linear or branched $C_1$-$C_{20}$, preferably $C_1$-$C_8$, alkoxy groups, optionally substituted phenoxy groups, or a cyano group;

or $R_1$ and $R_2$, may optionally be bound together so as to form, together with the carbon atoms to which they are bound, a saturated, unsaturated or aromatic cyclic or polycyclic system containing from 3 to 14 carbon atoms, preferably from 4 to 6 carbon atoms, optionally containing one or more heteroatoms such as, for example, oxygen, sulfur, nitrogen, silicon, phosphorus, selenium;

or $R_2$ and $R_3$, may optionally be bound together so as to form, together with the carbon atoms to which they are bound, a saturated, unsaturated or aromatic cyclic or polycyclic system containing from 3 to 14 carbon atoms, preferably from 4 to 6 carbon atoms, containing one or more heteroatoms such as, for example, oxygen, sulfur, nitrogen, silicon, phosphorus, selenium;

$R_4$, identical or different, represent a hydrogen atom; or are selected from linear or branched, preferably linear, $C_1$-$C_{20}$, preferably $C_1$-$C_8$, alkyl groups;

$R_5$, identical or different, are selected from linear or branched $C_1$-$C_{20}$, preferably $C_1$-$C_8$, alkyl groups optionally containing heteroatoms, optionally substituted cycloalkyl groups;

n and m, identical or different, are 0 or 1, provided that at least one of m and n is 1.

For the purpose of the present description and of the following claims, the definitions of numerical ranges always include the end members unless specified otherwise.

For the purpose of the present description and of the following claims, the term "comprising" also includes the terms "essentially consisting of" or "consisting of".

For the purpose of the present description and of the following claims, the term "$C_1$-$C_{20}$ alkyl groups" is intended to mean linear or branched alkyl groups having from 1 to 20 carbon atoms. Specific examples of $C_1$-$C_{20}$ alkyl groups are: methyl, ethyl, n-propyl, iso-propyl, n-butyl, iso-butyl, t-butyl, pentyl, 2-ethyl-hexyl, hexyl, heptyl, octyl, nonyl, decyl, dodecyl.

For the purpose of the present description and of the following claims, the term "$C_1$-$C_{20}$ alkyl groups optionally containing heteroatoms" is intended to mean linear or branched, saturated or unsaturated, alkyl groups having from 1 to 20 carbon atoms wherein at least one of the hydrogen atoms is substituted with a heteroatom selected from: halogens such as, for example, fluorine, chlorine, preferably fluorine; nitrogen; sulfur; oxygen. Specific examples of $C_1$-$C_{20}$ alkyl groups optionally containing heteroatoms are: fluoromethyl, difluoromethyl, trifluoromethyl, trichloromethyl, 2,2,2-trifluoroethyl, 2,2,2-trichlororoethyl, 2,2,3,3-tetrafluoropropyl, 2,2,3,3,3-pentafluoropropyl, perfluoropentyl, perfluoroctyl, perfluorodecyl, oxymethyl, thiomethyl, thioethyl, dimethylamino, dipropylamino, dioctylamino.

For the purpose of the present description and of the following claims the term "cycloalkyl groups" is intended to mean cycloalkyl groups having from 3 to 10 carbon atoms. Said cycloalkyl groups may be optionally substituted with one or more groups, identical or different, selected from: halogen atoms such as, for example, fluorine, chlorine, preferably fluorine; hydroxyl groups; $C_1$-$C_{20}$ alkyl groups; $C_1$-$C_{20}$ alkoxy groups; cyano groups; amine groups; nitro groups; aryl groups. Specific examples of cycloalkyl groups are: cyclopropyl, 1,4-dioxin, 2,2-difluorocyclopropyl, cyclobutyl, cyclopentyl, cyclohexyl, methylcyclohexyl, methoxycyclohexyl, fluorocyclohexyl, phenylcyclohexyl.

For the purpose of the present description and of the following claims, the term "aryl groups" is intended to mean aromatic carbocyclic groups. Said aryl groups may be optionally substituted with one or more groups, identical or different, selected from: halogen atoms such as, for example, fluorine, chlorine, preferably fluorine; hydroxyl groups; $C_1$-$C_{20}$ alkyl groups; $C_1$-$C_{20}$ alkoxy groups; cyano groups; dialkylamino groups; nitro groups; aryl groups. Specific examples of aryl groups are: phenyl, methylphenyl, dimethylphenyl, trimethylphenyl, di-iso-propylphenyl, t-butylphenyl, methoxyphenyl, hydroxyphenyl, phenyloxyphenyl, fluorophenyl, pentafluorophenyl, chlorophenyl, nitrophenyl, dimethylaminophenyl, naphthyl, phenylnaphthyl, phenanthrene, anthracene. For the purpose of the present description and of the following claims the term "$C_1$-$C_{20}$ alkoxy groups" is intended to mean linear or branched alkoxy groups having from 1 to 20 carbon atoms. Said alkoxy groups may be optionally substituted with one or more groups, identical or different, selected from: halogen atoms such as, for example, fluorine, chlorine, preferably fluorine; hydroxyl groups; $C_1$-$C_{20}$ alkyl groups; $C_1$-$C_{20}$ alkoxy groups; cyano groups; amino groups; nitro groups. Specific examples of $C_1$-$C_{20}$ alkoxy groups are: methoxy, ethoxy, fluoroethoxy, n-propoxy, iso-propoxy, n-butoxy, n-fluoro-butoxy, iso-butoxy, t-butoxy, pentoxy, hexyloxy, heptyloxy, octyloxy, nonyloxy, decyloxy, dodecyloxy.

For the purpose of the present description and of the following claims, the term "optionally substituted phenoxy groups" means $C_6H_5O$ phenoxy groups optionally substituted with one or more groups, identical or different, selected from: halogen atoms such as, for example, fluorine, chlorine, preferably fluorine; $C_1$-$C_{20}$ alkyl groups; $C_1$-$C_{20}$ alkoxy groups; cyano groups; amino groups; nitro groups. Specific examples of $C_6H_5O$ phenoxy groups are: phenoxy, 4-nitrophenoxy, 2,4-di-nitrophenoxy, 2-chloro-4-nitrophenoxy, 2-fluoro-4-nitrophenoxy, 3-fluoro-4-nitrophenoxy, 5-fluoro-2-nitrophenoxy, 2-dimethyl-aminophenoxy.

In accordance with a preferred embodiment of the present invention, in said general formula (I) or (II):

Z represents a sulfur atom;
$R_1$, mutually identical, represent a hydrogen atom; or are selected from optionally substituted aryl groups, preferably are 2,6-dimethylphenyl, 2,5-dimethylphenyl;
$R_2$ and $R_3$, mutually identical, represent a hydrogen atom;
$R_4$, mutually identical, are selected from linear or branched $C_1$-$C_8$ alkyl groups, preferably are methyl;
$R_5$, mutually identical, are selected from linear or branched $C_1$-$C_8$ alkyl groups, preferably are methyl;
n and m, identical or different, are 0 or 1, provided that at least one of n and m is 1.

Specific examples of disubstituted diaryloxybenzoheterodiazole compounds having general formula (I) which are useful for the purpose of the present invention are shown in Table 1.

TABLE 1

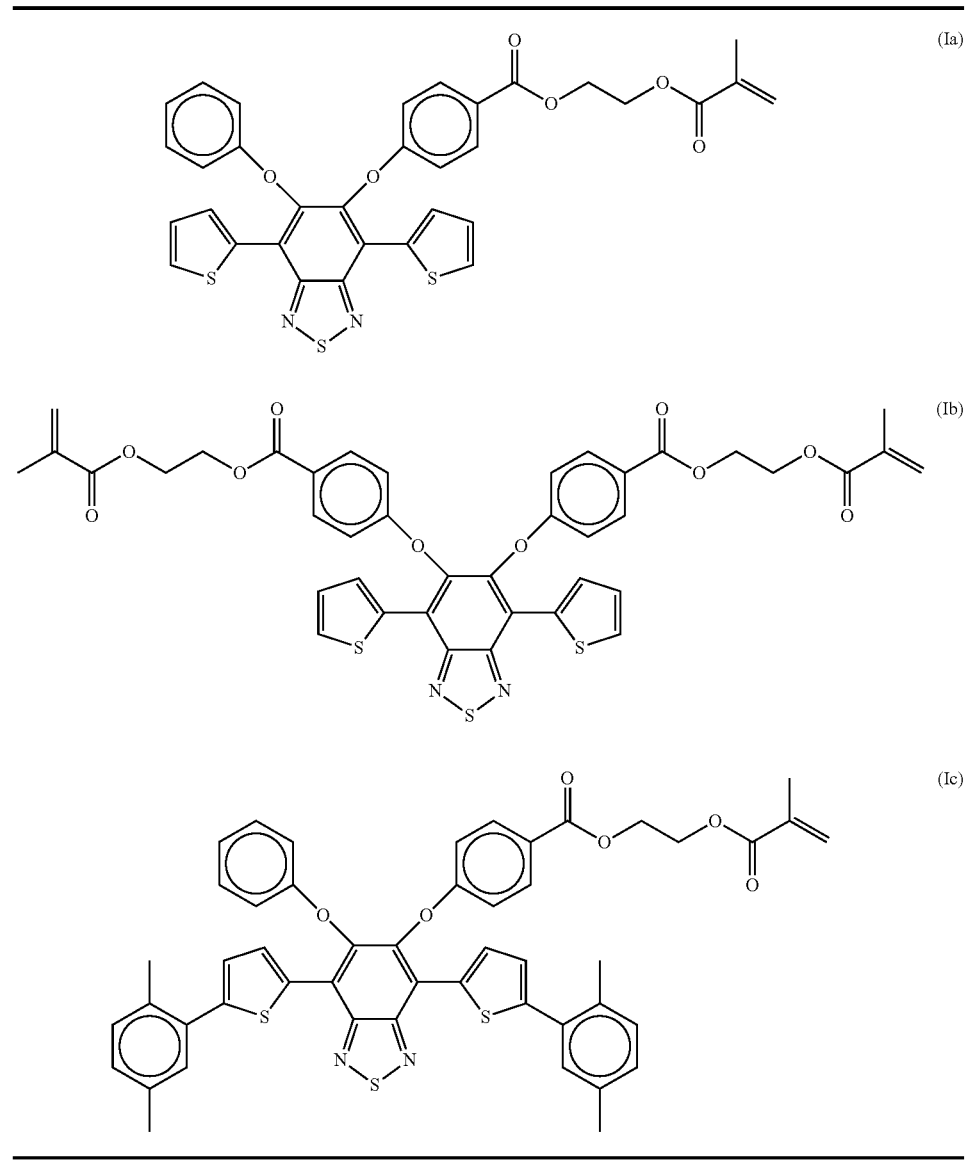

Specific examples of disubstituted diaryloxybenzoheterodiazole compounds having general formula (II) which are useful for the purpose of the present invention are shown in Table 2.

TABLE 2

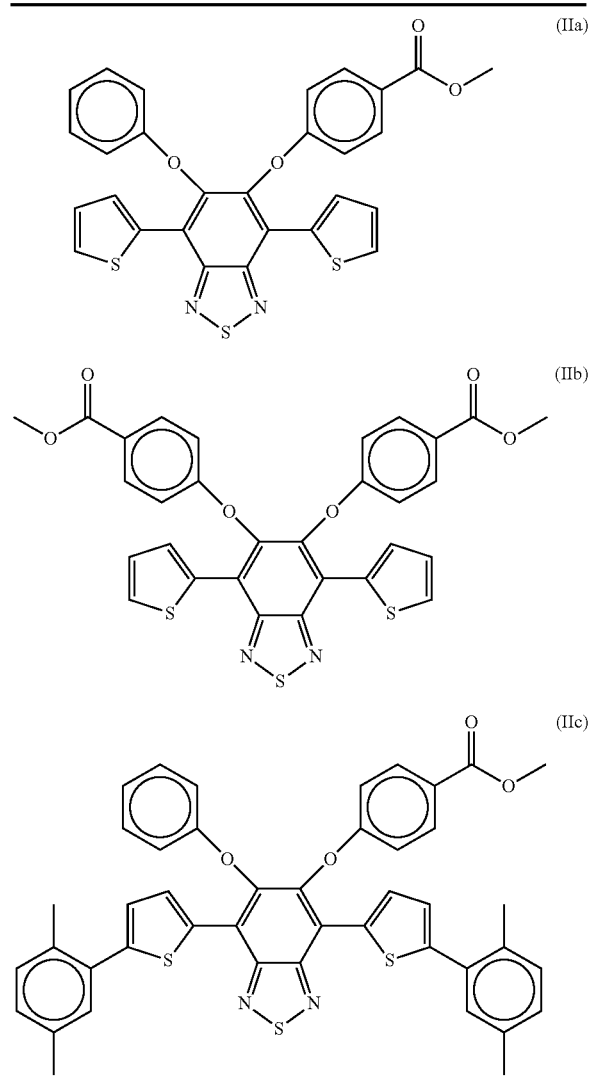

TABLE 2-continued

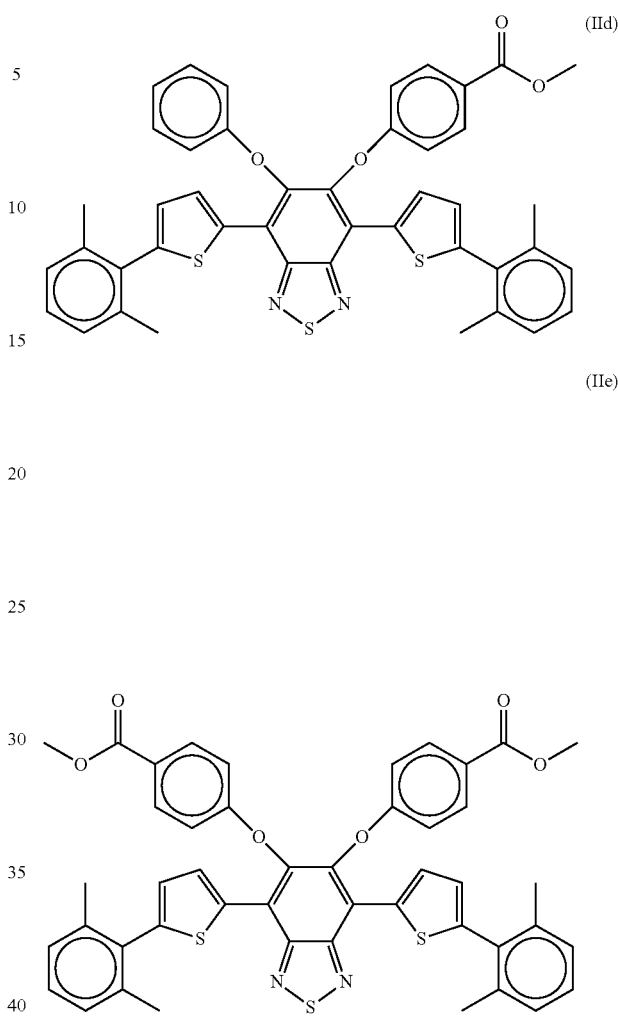

The present invention also relates to processes for the preparation of disubstituted diaryloxybenzoheterodiazole compounds having general formula (I) or (II).

A further object of the present invention is therefore a process for the preparation of a disubstituted diaryloxybenzoheterodiazole compound having general formula (I):

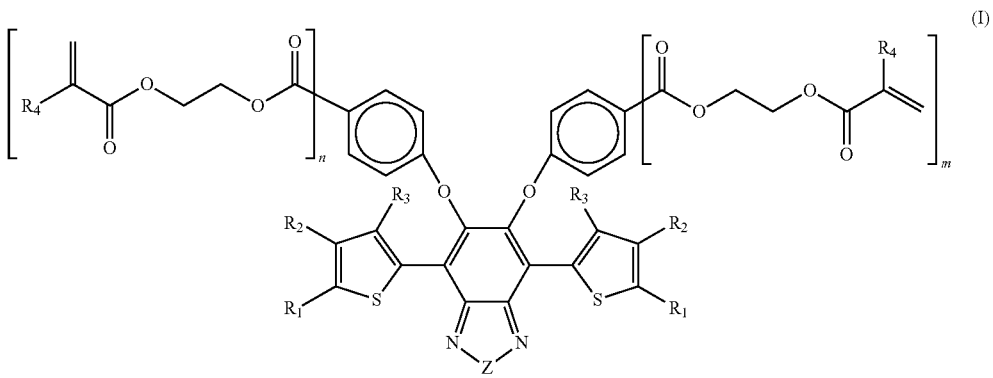

wherein Z, $R_1$, $R_2$, $R_3$, $R_4$, m and n have the same meanings as described above, comprising reacting at least one acid of a disubstituted diaryloxybenzoheterodiazole compound having general formula (III):

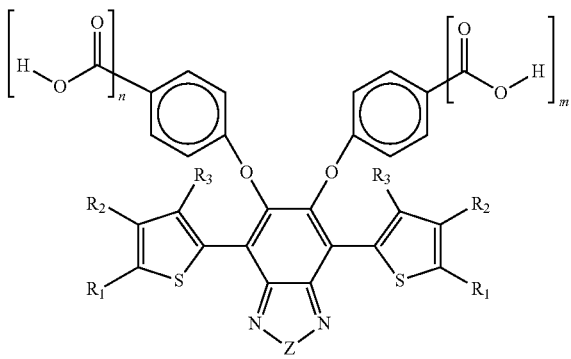

(III)

wherein Z, $R_1$, $R_2$, $R_3$, m and n have the same meanings as described above, with at least one hydroxyalkyl (meth)acrylate in the presence of at least one carbodiimide and at least one dialkyl-aminopyridine.

In accordance with a preferred embodiment of the present invention, said hydroxyalkyl (meth)acrylate may be selected, for example, from: 2-hydroxyethyl acrylate, 2-hydroxyethyl methacrylate (HEMA), 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate, 3-hydroxy-2-ethylhexyl methacrylate, neopentyl glycol monoacrylate, neopentyl glycol monomethacrylate, 1,5-pentanediol monoacrylate, 1,5-pentanediol monomethacrylate, 1,6-hexanediol monoacrylate, 1,6-hexanediol monomethacrylate, or mixtures thereof, 2-hydroxyethyl methacrylate (HEMA), 2-hydroxypropyl methacrylate are preferred, 2-hydroxyethyl methacrylate (HEMA) is particularly preferred.

In accordance with a preferred embodiment of the present invention, said acid of a disubstituted diaryloxybenzoheterodiazole compound having general formula (III) and said hydroxyalkyl (meth)acrylate may be used in molar ratios ranging from 1:3 to 1:15, preferably ranging from 1:3 to 1:8.

In accordance with a preferred embodiment of the present invention, said carbodiimide may be selected, for example, from: water-insoluble carbodiimides such as, for example, dicyclohexylcarbodiimide (DCC), diisopropylcarbodiimide; or from water-soluble carbodiimides such as, for example, 1-ethyl-[3-(3-dimethylamino)propyl]-carbodiimide hydrochloride (WSC). Dicyclohexylcarbodiimide (DCC), 1-ethyl-[3-(3-dimethylamino)propyl]-carbodiimide hydrochloride (WSC) are preferred, 1-ethyl-[3-(3-dimethylamino)propyl]-carbodiimide hydrochloride (WSC) is particularly preferred.

In accordance with a preferred embodiment of the present invention, said acid of a disubstituted diaryloxybenzoheterodiazole compound having general formula (III) and said carbodiimide may be used in molar ratios ranging from 1:1 to 1:5, preferably ranging from 1:1 to 1:3.

In accordance with a preferred embodiment of the present invention, said dialkyl-aminopyridine may be selected, for example, from: N,N-dimethyl-4-aminopyridine (DMPA), N,N-diethyl-4-aminopyridine, N,N-dibutyl-4-aminopyridine. N,N-dimethyl-4-aminopyridine (DMPA) is preferred.

In accordance with a preferred embodiment of the present invention, said acid of a disubstituted diaryloxybenzoheterodiazole compound having general formula (III) and said dialkyl-aminopyridine may be used in molar ratios ranging from 1:0.1 to 1:2, preferably ranging from 1:0.2 to 1:1.

In accordance with a preferred embodiment of the present invention, said process may be carried out in the presence of at least one organic solvent which may be selected, for example, from: ethers such as, for example, 1,2-dimethoxyethane, 1,4-dioxane, tetrahydrofuran, or mixtures thereof; hydrocarbons such as, for example, toluene, xylene, or mixtures thereof; solvent esters such as, for example, methyl acetate, ethyl acetate, or mixtures thereof; dipolar aprotic solvents such as, for example, N,N-dimethylformamide, N-methylpyrrolidone, dimethylsulfoxide, or mixtures thereof; chlorinated solvents such as, for example, dichloromethane, dichloroethane, dichlorobenzene, or mixtures thereof; or mixtures thereof, preferably dichloromethane, more preferably anhydrous dichloromethane.

In accordance with a preferred embodiment of the present invention, said acid of a disubstituted diaryloxybenzoheterodiazole compound having general formula (III) may be used in said organic solvent in such a quantity as to have a molar concentration in said organic solvent ranging from 0.005 M to 2 M, preferably ranging from 0.01 M to 0.1 M.

In accordance with a preferred embodiment of the present invention, said process may be carried out at a temperature ranging from −40° C. to 40° C., preferably ranging from 0° C. to 30° C.

In accordance with a preferred embodiment of the present invention, said process may be carried out for a time ranging from 1 hour to 30 hours, preferably ranging from 2 hours to 20 hours.

Generally, the mixture obtained at the end of the aforesaid process is poured into water and extracted with dichloromethane obtaining an organic phase which is washed to neutral first with a saturated aqueous solution of ammonium chloride, then with a saturated aqueous solution of sodium bicarbonate and finally with brine and subsequently dried on sodium sulfate. The residual solvent is then removed (for example, by distillation under reduced pressure) and the residue obtained is purified using normal methods of purification such as, for example, elution on a silica gel, neutral alumina, or basic alumina, preferably neutral alumina or basic alumina chromatography column, and/or crystallization from organic solvents such as, for example: hydrocarbons (e.g., n-heptane, hexane, toluene, or mixtures thereof); chlorinated solvents (e.g., dichloromethane, chloroform, or mixtures thereof); solvent esters (e.g., methyl acetate, ethyl acetate, methyl propionate, or mixtures thereof); solvent ethers (e.g., ethyl ether, tetrahydrofuran, t-butylmethylether, or mixtures thereof); alcohols (e.g., methanol, ethanol, propanol, or mixtures thereof); or mixtures thereof.

The acids of disubstituted diaryloxybenzoheterodiazole compounds having general formula (III) may be obtained by saponification of the corresponding ester or disubstituted diaryloxybenzoheterodiazole compounds having general formula (II), operating in accordance with procedures known in the art, as described, for example, by Wang, L.-Y. et al., in "Macromolecules" (2010), Vol. 43, p. 1277-1288. In this respect, at least one disubstituted diaryloxybenzoheterodiazole compound having general formula (II) is caused to react with at least one alkali metal hydroxide selected, for example, from sodium hydroxide, potassium hydroxide, lithium hydroxide, preferably sodium hydroxide, potassium hydroxide. Preferably, said disubstituted diaryloxybenzoheterodiazole compound having general formula (II) and said alkali metal hydroxide may be used in molar ratios ranging from 1:1 to 1:30, preferably ranging from 1:1 to 1:15.

Preferably, said reaction is carried out in the presence of at least one alcohol selected, for example, from: methanol, ethanol, propanol, butanol, iso-propanol, iso-butanol, pentanol, 3-methyl-1-butanol, or mixtures thereof, preferably ethanol. Said alcohol may also be used in a mixture with water. Preferably, said reaction is carried out at a temperature ranging from 20° C. to 100° C., more preferably ranging from 40° C. to 90° C., for a time ranging from 1 hour to 14 hours, preferably ranging from 3 hours to 12 hours.

The disubstituted diaryloxybenzoheterodiazole compounds having general formula (II) may be obtained using the processes described below.

Thus a further object of the present invention is a first process for preparing a disubstituted diaryloxybenzoheterodiazole compound having general formula (II):

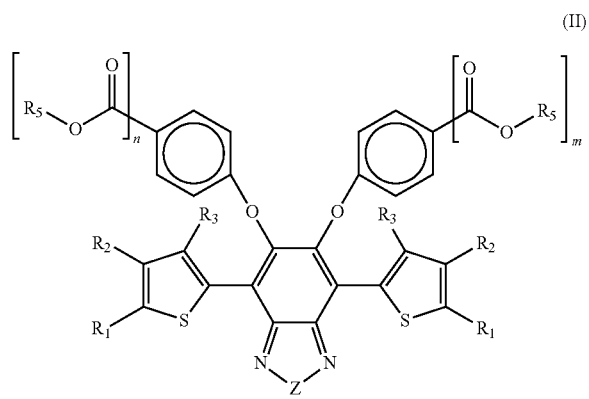

(II)

wherein Z, $R_1$, $R_2$, $R_3$ and $R_5$, have the same meanings as described above, and n and m are equal to 1, comprising:
(a) causing at least one disubstituted fluorinated benzoheterodiazole compound having general formula (IV):

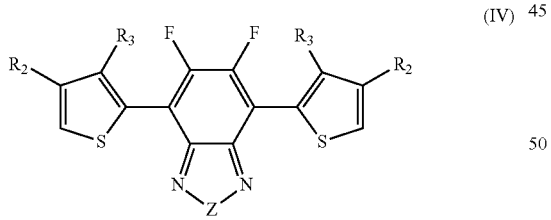

(IV)

wherein Z, $R_2$ and $R_3$, have the same meanings as described above, to react with at least one alkyl 4-hydroxybenzoate having general formula (V):

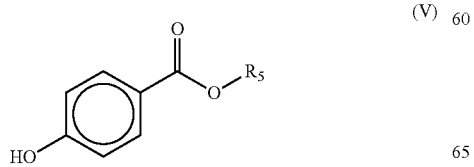

(V)

wherein $R_5$ has the same meanings as described above, obtaining a disubstituted diaryloxybenzoheterodiazole compound having general formula (VI):

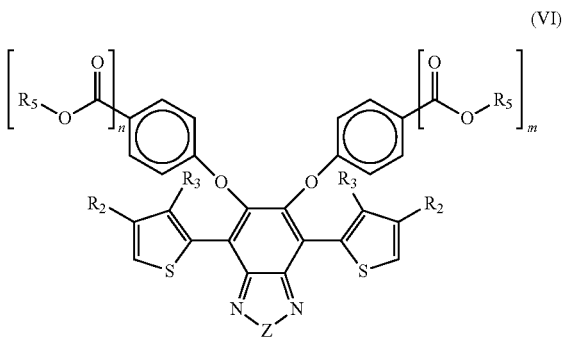

(VI)

wherein Z, $R_2$, $R_3$ and $R_5$ have the same meanings as described above, and n and m are equal to 1; and in the case where, in the disubstituted diaryloxybenzoheterodiazole compound having general formula (II), $R_1$, identical or different, do not represent hydrogen atoms,
(b) causing at least one disubstituted diaryloxybenzoheterodiazole compound having general formula (VI) obtained in step (a) to react with at least one compound selected from N-haloimides such as, for example, N-bromosuccinimide, N-bromophthalimide, N-iodosuccinimide, N-iodophthalimide, obtaining a disubstituted halogenated diaryloxybenzoheterodiazole compound having general formula (VII):

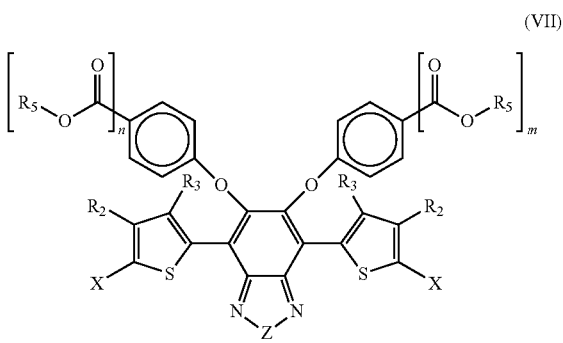

(VII)

wherein Z, $R_2$, $R_3$ and $R_5$ have the same meanings as described above, and X is a halogen atom selected from bromine, iodine, preferably bromine;
(c) causing at least one disubstituted halogenated diaryloxybenzoheterodiazole compound having general formula (VII) obtained in step (b) to react with at least one aryl-boron compound having general formula VIII):

(VIII)

wherein $R_1$ has the same meanings as described above provided that the $R_1$ substituent does not represent a hydrogen atom and the $R_7$ substituents represent a hydrogen atom, or may be selected from linear or branched $C_1$-$C_{10}$ alkyl groups, or from optionally substituted cycloalkyl groups, or the two $R_7$ substituents may optionally be bound together so as to form, together with the other atoms to which they are bound, a cyclic compound as in the case of the pinacol esters of boronic acid or of the 1,3-propandiol esters of boronic acid.

In accordance with a preferred embodiment of the present invention, in said step (a) said disubstituted fluorinated benzoheterodiazole compound having general formula (IV) and said alkyl 4-hydroxybenzoate having general formula (V) may be used in molar ratios ranging from 1:2 to 1:10, preferably ranging from 1:2 to 1:5.

In accordance with a preferred embodiment of the present invention, said step (a) may be carried out in the presence of at least one weak organic base which may be selected, for example, from: alkali metal (e.g., sodium, potassium, cesium) or alkaline-earth metal (e.g., magnesium, calcium) carboxylates such as, for example, potassium acetate, sodium acetate, cesium acetate, magnesium acetate, calcium acetate, potassium propionate, sodium propionate, cesium propionate, magnesium propionate, calcium propionate, or mixtures thereof; alkali metal (e.g., lithium, sodium, potassium, cesium) or alkaline-earth metal (e.g., magnesium, calcium) carbonates such as, for example, lithium carbonate, potassium carbonate, sodium carbonate, cesium carbonate, magnesium carbonate, calcium carbonate, or mixtures thereof; alkali metal (e.g., lithium, sodium, potassium, cesium) or alkaline-earth metal (e.g., magnesium, calcium) bicarbonates such as, for example, lithium bicarbonate, potassium bicarbonate, sodium bicarbonate, cesium bicarbonate, magnesium bicarbonate, calcium bicarbonate or mixtures thereof; or mixtures thereof; preferably potassium carbonate, sodium carbonate, cesium carbonate. Preferably, said disubstituted fluorinated benzoheterodiazole compound having general formula (IV) and said weak organic base may be used in molar ratios ranging from 1:1 to 1:10, preferably ranging from 1:2 to 1:5.

In accordance with a preferred embodiment of the present invention, said step (a) may be carried out in the presence of at least one organic solvent which may be selected, for example, from: ethers such as, for example, 1,2-dimethoxyethane, 1,4-dioxane, tetrahydrofuran, or mixtures thereof; chlorinated solvents such as, for example, dichloromethane, chloroform, or mixtures thereof; dipolar aprotic solvents such as, for example, N,N-dimethylformamide, N-methylpyrrolidone, dimethyl sulfoxide, or mixtures thereof; preferably N,N-dimethylformamide.

In accordance with a preferred embodiment of the present invention, said disubstituted fluorinated benzoheterodiazole compound having general formula (IV) may be used in said organic solvent in such a quantity as to have a molar concentration in said organic solvent ranging from 0.05 M to 2 M, preferably ranging from 0.1 M to 1 M.

In accordance with a preferred embodiment of the present invention, said step (a) may be carried out at a temperature ranging from 60° C. to 150° C., preferably ranging from 80° C. to 120° C.

In accordance with a preferred embodiment of the present invention, said step (a) may be carried out for a time ranging from 1 hour to 24 hours, preferably ranging from 2 hours to 18 hours.

In accordance with a preferred embodiment of the present invention, in said step (b) said disubstituted diaryloxybenzoheterodiazole compound having general formula (VI) and said compound selected from N-haloimides may be used in molar ratios ranging from 1:2 to 1:3, preferably ranging from 1:2 to 1:2.5.

In accordance with a preferred embodiment of the present invention, said step (b) may be carried out in the presence of at least one organic solvent which may be selected, for example, from: ethers such as, for example, 1,2-dimethoxyethane, 1,4-dioxane, tetrahydrofuran, or mixtures thereof; chlorinated solvents such as, for example, dichloromethane, chloroform, or mixtures thereof; dipolar aprotic solvents such as, for example, N,N-dimethylformamide, N-methylpyrrolidone, dimethylsulfoxide or mixtures thereof; preferably tetrahydrofuran.

In accordance with a preferred embodiment of the present invention, said disubstituted diaryloxybenzoheterodiazole compound having general formula (VI) may be used in said organic solvent in such a quantity as to have a molar concentration in said organic solvent ranging from 0.01 M to 5 M, preferably ranging from 0.02 M to 2 M.

In accordance with a preferred embodiment of the present invention, said step (b) may be carried out at a temperature ranging from 20° C. to 50° C., preferably ranging from 22° C. to 30° C.

In accordance with a preferred embodiment of the present invention, said step (b) may be carried out for a time ranging from 1 hour to 24 hours, preferably ranging from 4 hours to 18 hours.

Generally, at the end of said step (b) the mixture obtained, after the addition of distilled water, is subjected to filtration obtaining a residue, which is washed with distilled water to remove all the imide formed during the reaction and the product obtained may be used as such in step (c).

For the purpose of the present invention said step (c) may be carried out according to the Suzuki reaction.

In accordance with one embodiment of the present invention, in said step (c) said disubstituted halogenated diaryloxybenzoheterodiazole compound having general formula (VII) and said aryl boron compound having general formula (VIII), may be used in molar ratios ranging from 1:2 to 1:5, preferably ranging from 1:2 to 1:4.

In accordance with a preferred embodiment of the present invention, said step (c) may be carried out in the presence of at least one catalyst containing palladium which maybe selected, for example, from palladium compounds in oxidation state (0) or (II), such as, for example, palladium-tetrakistriphenylphosphine [Pd(PPh$_3$)$_4$], bis-triphenylphosphine palladium dichloride [PdCl$_2$(PPh$_3$)$_2$], preferably palladium-tetrakistriphenylphosphine [Pd(PPh$_3$)$_4$]. Preferably, said disubstituted halogenated diaryloxybenzoheterodiazole compound having general formula (VII) and said catalyst may be used in molar ratios ranging from 1:0.15 to 1:0.01, preferably ranging from 1:0.02 to 1:0.12.

In accordance with a preferred embodiment of the present invention, said step (c) may be carried out in the presence of at least one weak organic base which may be selected, for example, from: alkali metal (e.g., sodium, potassium, cesium) or alkaline-earth metal (e.g., magnesium, calcium) carboxylates such as, for example, potassium acetate, sodium acetate, cesium acetate, magnesium acetate, calcium acetate, potassium propionate, sodium propionate, cesium propionate, magnesium propionate, calcium propionate, or mixtures thereof; alkali metal (e.g., lithium, sodium, potassium, cesium) or alkaline-earth metal (e.g., magnesium, calcium) carbonates such as, for example, lithium carbonate, potassium carbonate, sodium carbonate, cesium carbonate, magnesium carbonate, calcium carbonate, or mixtures thereof; alkali metal (e.g., lithium, sodium, potassium, cesium) or alkaline-earth metal (e.g., magnesium, calcium) bicarbonates such as, for example, lithium bicarbonate, potassium bicarbonate, sodium bicarbonate, cesium bicarbonate, magnesium bicarbonate, calcium bicarbonate, or mixtures thereof; or mixtures thereof; preferably potassium carbonate, sodium carbonate, cesium carbonate. In said step (c), said base may be used as such, or in aqueous solution. Preferably, said disubstituted halogenated diaryloxybenzoheterodiazole compound having general formula (VII) and said weak organic base may be used in molar ratios ranging from 1:1 to 1:20, preferably ranging from 1:2 to 1:10.

In accordance with a preferred embodiment of the present invention, said step (c) may be carried out in the presence of at least one organic solvent which may be selected, for example, from: ethers such as, for example, 1,2-dimethoxyethane, 1,4-dioxane, tetrahydrofuran, or mixtures thereof; hydrocarbons such as, for example, toluene, xylene, or mixtures thereof; dipolar aprotic solvents such as, for example, N,N-dimethylformamide, N-methylpyrrolidone, dimethylsulfoxide, or mixtures thereof; or mixtures thereof; preferably 1,4-dioxane. In said step (b) said organic solvent may also be used in a mixture with at least one alcohol such as, for example, methanol, ethanol, n-propanol, iso-propanol, or mixtures thereof.

In accordance with a preferred embodiment of the present invention, said disubstituted halogenated diaryloxybenzoheterodiazole compound having general formula (VII) may be used in said organic solvent in such a quantity as to have a molar concentration in said organic solvent ranging from 0.01 M to 2 M, preferably ranging from 0.02 M to 1 M.

In accordance with a preferred embodiment of the present invention, said step (c) may be carried out at a temperature ranging from 50° C. to 140° C., preferably ranging from 60° C. to 120° C.

In accordance with a preferred embodiment of the present invention, said step (c) may be carried out for a time ranging from 2 hours to 36 hours, preferably ranging from 4 hours to 18 hours.

Generally, at the end of the aforesaid process, the mixture obtained, after the addition of distilled water, is extracted with an organic solvent (for example, dichloromethane) obtaining an organic phase which is washed to neutral (for example, with distilled water) and dried (for example, on sodium sulfate). The residual solvent is then removed (for example, by distillation under reduced pressure) and the residue obtained is purified using normal laboratory techniques (for example, elution on a chromatography column and/or crystallization, working as described above).

Yet another object of the present invention is a second process for preparing a disubstituted diaryloxybenzoheterodiazole compound having general formula (II):

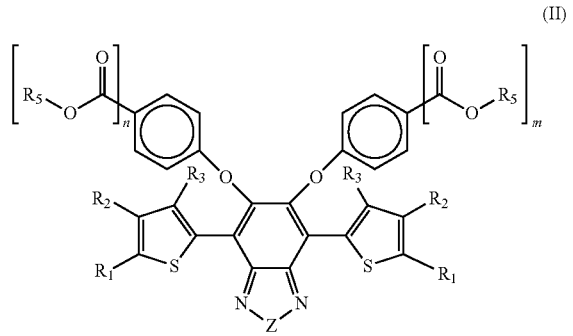

(II)

wherein Z, $R_1$, $R_2$, $R_3$ and $R_5$ have the same meanings as described above, and if n is 0 m is 1 or vice versa, comprising:

($a_1$) causing at least one disubstituted fluorinated benzoheterodiazole compound having general formula (IV):

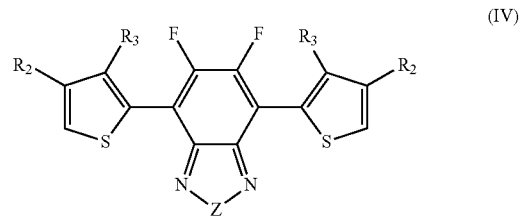

(IV)

wherein Z, $R_2$ and $R_3$ have the same meanings as described above, to react with at least one alkyl 4-hydroxybenzoate having general formula (V):

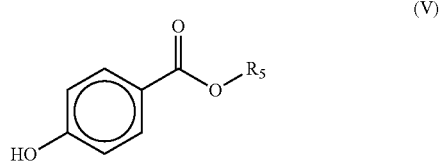

(V)

wherein $R_5$ has the same meanings as described above, said disubstituted fluorinated benzoheterodiazole compound having general formula (IV) and said alkyl 4-hydroxybenzoate having general formula (V) being used in equal molar ratios, obtaining a reaction mixture comprising at least one disubstituted fluorinated monoaryloxybenzoheterodiazole compound having general formula (VIa):

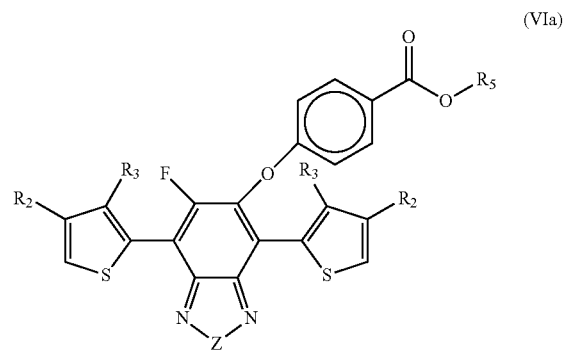

(VIa)

wherein Z, $R_2$, $R_3$ and $R_5$ have the same meanings as described above, and m is 1;

($b_1$) adding directly to the reaction mixture obtained in step ($a_1$) at least one phenol having formula (IX), said phenol having formula (IX) being used in equal molar ratios or in molar excess with respect to said disubstituted fluorinated benzoheterodiazole compound having general formula (IV):

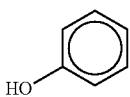 (IX)

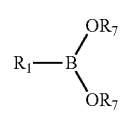 (VIII)

wherein $R_1$ has the same meanings as described above, provided that the $R_1$ substituent does not represent a hydrogen atom, and the $R_7$ substituents represent a hydrogen atom or are selected from linear or branched $C_1$-$C_{10}$ alkyl groups, or from optionally substituted cycloalkyl groups, or the two $R_7$ substituents may optionally be bound together so as to form, together with the other atoms to which they are bound, a cyclic compound as in the case of the pinacol esters of boronic acid or of the 1,3-propanediol esters of boronic acid.

It should be noted that, for the purpose of the present invention, said disubstituted fluorinated monoaryloxybenzoheterodiazole compound having general formula (VIa) may optionally be isolated from the reaction mixture obtained in said step ($a_1$) and subsequently caused to react with at least one phenol having formula (IX), said phenol having formula (IX) being used in equal molar ratios or in molar excess with respect to said disubstituted fluorinated monoaryloxybenzoheterodiazole compound having general formula (VIa).

In accordance with a preferred embodiment of the present invention, said step ($a_1$) may be carried out in the presence of at least one weak organic base which may, for example, be selected from: alkali metal (e.g., sodium, potassium, cesium) or alkaline-earth metal (e.g., magnesium, calcium) carboxylates such as, for example, potassium acetate, sodium acetate, cesium acetate, magnesium acetate, calcium acetate, potassium propionate, sodium propionate, cesium propionate, magnesium propionate, calcium propionate, or mixtures thereof; alkali metal (e.g., lithium, sodium, potassium, cesium) or alkaline-earth metal (e.g., magnesium, calcium) carbonates such as, for example, lithium carbonate, potassium carbonate, sodium carbonate, cesium carbonate, magnesium carbonate, calcium carbonate, or mixtures thereof; alkali metal (e.g., lithium, sodium, potassium, cesium) or alkaline-earth metal (e.g., magnesium, calcium) bicarbonates such as, for example, lithium bicarbonate, potassium bicarbonate, sodium bicarbonate, cesium bicarbonate, magnesium bicarbonate, calcium bicarbonate, or mixtures thereof; or mixtures thereof; preferably potassium carbonate, sodium carbonate, cesium carbonate. Preferably, said disubstituted fluorinated benzoheterodiazole compound having general formula (IV) and said weak organic base may be used in molar ratios ranging from 1:1 to 1:10, preferably ranging from 1:1 to 1:5.

In accordance with a preferred embodiment of the present invention, said step ($a_1$) may be carried out in the presence of at least one organic solvent which may be selected, for example, from: ethers such as, for example, 1,2-dimethoxyethane, 1,4-dioxane, tetrahydrofuran, or mixtures thereof; chlorinated solvents such as, for example, dichloromethane, chloroform, or mixtures thereof; dipolar aprotic solvents such as, for example, N,N-dimethylformamide, N-methylpyrrolidone, dimethylsulfoxide; or mixtures thereof; preferably N,N-dimethylformamide.

In accordance with a preferred embodiment of the present invention, said disubstituted fluorinated benzoheterodiazole compound having general formula (IV) may be used in said organic solvent in such a quantity as to have a molar obtaining a disubstituted diaryloxybenzoheterodiazole compound having general formula (X):

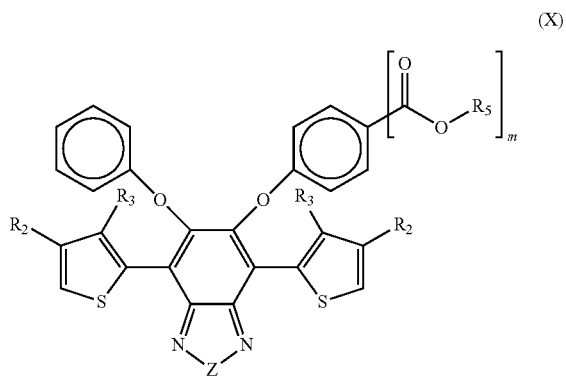 (X)

wherein Z, $R_2$, $R_3$ and $R_5$ have the same meanings as described above and m is 1; and in case where, in the disubstituted diaryloxybenzoheterodiazole compound having general formula (II), $R_1$, identical or different, do not represent hydrogen atoms, ($c_1$) causing at least one disubstituted diaryloxybenzoheterodiazole compound having general formula (X) obtained in step ($b_1$) to react with at least one compound selected from N-haloimides such as, for example, N-bromosuccinimide, N-bromophthalimide, N-iodosuccinimide, N-iodophthalimide, obtaining a disubstituted halogenated diaryloxybenzoheterodiazole compound having general formula (XI):

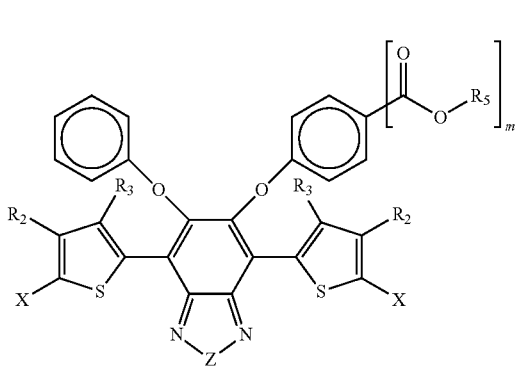 (XI)

wherein Z, $R_2$, $R_3$ and $R_5$ have the same meanings as described above, and X is a halogen atom selected from bromine, iodine, preferably bromine;

($d_1$) causing at least one disubstituted halogenated diaryloxybenzoheterodiazole compound having general formula (XI) obtained in step ($c_1$) to react with at least one aryl-boron compound having general formula (VIII):

concentration in said organic solvent ranging from 0.05 M to 2 M, preferably ranging from 0.1 M to 1 M.

In accordance with a preferred embodiment of the present invention, both said step ($a_1$) and said step ($b_1$) may be carried out separately at a temperature ranging from 60° C. to 150° C., preferably ranging from 80° C. to 100° C.

In accordance with a preferred embodiment of the present invention, both said step ($a_1$) and said step ($b_1$), independently, may be carried out for a time ranging from 1 hour to 24 hours, preferably ranging from 1 hour to 12 hours.

Generally, at the end of said step ($b_1$), the mixture obtained, after the addition of distilled water, may be subjected to filtration obtaining a solid residue which is washed with water, or may be extracted with an organic solvent (for example, dichloromethane) obtaining an organic phase which is washed to neutral (for example, with distilled water) and dried (for example, on sodium sulfate). The residual solvent is then removed (for example, by distillation under reduced pressure) and the residue obtained is purified using normal laboratory techniques (for example, elution on a chromatography column and/or crystallization, working as described above).

The aforesaid steps ($c_1$) and ($d_1$), independently, may be carried out under the same operating conditions as described above for steps (b) and (c).

Generally, at the end of the aforesaid process, the mixture obtained, after the addition of distilled water, is extracted with an organic solvent (for example, dichloromethane) obtaining an organic phase which is washed to neutral (for example, with distilled water) and dried (for example, on sodium sulfate). The residual solvent is then removed (for example, by distillation under reduced pressure) and the residue obtained is purified using normal laboratory techniques (for example, elution on a chromatography column and/or crystallization, working as described above).

It should be noted that, by working in accordance with said second process for preparing a disubstituted diaryloxybenzoheterodiazole compound having general formula (II), it is also possible to prepare the disubstituted diaryloxybenzoheterodiazole compounds having general formula (XII) indicated below.

Thus, a further object of the present invention, is a process for preparing a disubstituted diaryloxybenzoheterodiazole compound having general formula (XII):

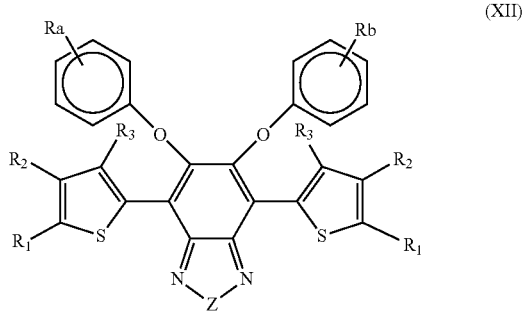

(XII)

wherein Z, $R_1$, $R_2$ and $R_3$ have the same meanings as described above, $R_a$ and $R_b$, which are different, represent a hydrogen atom; or are selected from linear or branched $C_1$-$C_{20}$, preferably $C_1$-$C_8$, alkyl groups optionally containing heteroatoms, optionally substituted cycloalkyl groups, optionally substituted aryl groups, optionally substituted linear or branched $C_1$-$C_{20}$, preferably $C_1$-$C_8$, alkoxy groups, optionally substituted phenoxy groups, —COOR$_c$ groups wherein Re is selected from linear or branched $C_1$-$C_{20}$, preferably $C_1$-$C_8$, alkyl groups, —CON(R$_c$)$_2$ groups wherein Re has the same meanings as described above, —N(R$_c$)$_2$ groups wherein Re has the same meanings as described above, comprising:

($a'_1$) causing at least one disubstituted fluorinated benzoheterodiazole compound having general formula (IV):

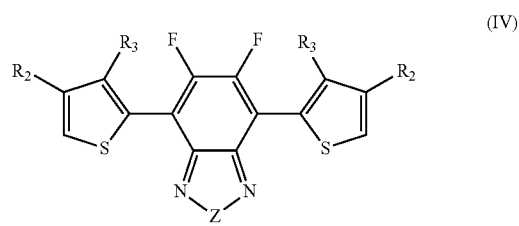

(IV)

wherein Z, $R_2$ and $R_3$ have the same meanings as described above, to react with at least one substituted phenol having general formula (XIII):

(XIII)

wherein $R_b$ has the same meanings as described above, said disubstituted fluorinated benzoheterodiazole compound having general formula (IV) and said substituted phenol having general formula (XIII) being used in equal molar ratios, obtaining a reaction mixture comprising at least one disubstituted fluorinated monoaryloxybenzoheterodiazole compound having general formula (XIIa):

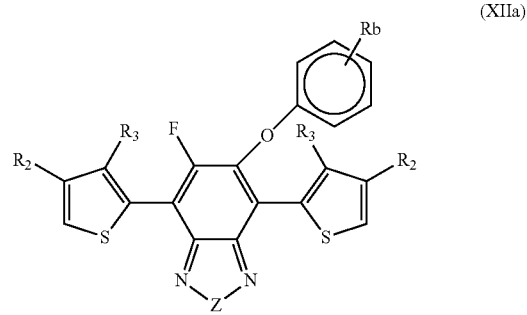

(XIIa)

wherein Z, $R_2$, $R_3$ and $R_b$ have the same meanings as described above;

($b'_1$) adding directly to the reaction mixture obtained in step ($a'_1$) at least one substituted phenol having general formula (XIV), said substituted phenol having general formula (XIV) being used in equal molar ratios or in molar excess with respect to said disubstituted fluorinated benzoheterodiazole compound having general formula (IV):

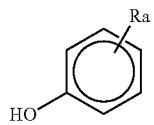
(XIV)

wherein $R_a$ has the same meanings as described above, obtaining a disubstituted diaryloxybenzoheterodiazole compound having general formula (XV):

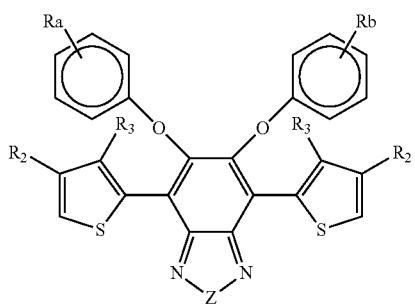
(XV)

wherein Z, $R_1$, $R_2$, $R_3$, $R_a$ and $R_b$ have the same meanings as described above; and in case where, in the disubstituted diaryloxybenzoheterodiazole compound having general formula (XII), $R_1$, identical or different, do not represent hydrogen atoms, (c'$_1$) causing at least one disubstituted diaryloxybenzoheterodiazole compound having general formula (XV) obtained in step (b'$_1$) to react with at least one compound selected from N-haloimides such as, for example, N-bromosuccinimide, N-bromophthalimide, N-iodosuccinimide, N-iodophthalimide, obtaining a disubstituted halogenated diaryloxybenzoheterodiazole compound having general formula (XVI):

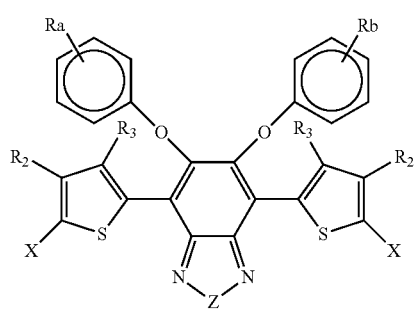
(XVI)

wherein Z, $R_1$, $R_2$, $R_3$, $R_a$ and $R_b$ have the same meanings as described above, and X is a halogen atom selected from bromine, iodine, preferably bromine;

(d'$_1$) causing at least one disubstituted halogenated diaryloxybenzoheterodiazole compound having general formula (XVI) obtained in step (c'$_1$) to react with at least one aryl-boron compound having general formula (VIII):

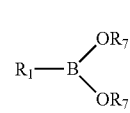
(VIII)

wherein $R_1$ has the same meaning as described above provided that the $R_1$ substituent does not represent a hydrogen atom, and the $R_7$ substituents do represent a hydrogen atom, or are selected from linear or branched $C_1$-$C_{10}$ alkyl groups, or from optionally substituted cycloalkyl groups, or the two $R_7$ substituents may optionally be bound together so as to form, together with the other atoms to which they are bound, a cyclic compound as in the case of the pinacol esters of boronic acid or of the 1,3-propanediol esters of boronic acid.

The aforesaid steps (a'$_1$)-(d'$_1$), independently, may be carried out under the same operating conditions as described above for steps (a$_1$)-(d$_1$).

It should be noted that, for the purpose of the present invention, said disubstituted fluorinated monoaryloxybenzoheterodiazole compound having general formula (XIIa) may be isolated from the reaction mixture obtained in said step (a$_1$) and subsequently caused to react with at least one substituted phenol having general formula (XIV), said substituted phenol having formula (XIV) being used in equal molar ratios or in molar excess with respect to said disubstituted fluorinated monoaryloxybenzoheterodiazole compound having general formula (XIIa).

The disubstituted fluorinated benzoheterodiazole compounds having general formula (IV) may be obtained according to processes known in the art as described, for example, by Kularatne, R. S. et al., in "*Journal of Materials Chemistry A*" (2013), Vol. 1(48), p. 15535-15543, or by Wang N. et al., in "*Journal of the American Chemical Society*" (2013), Vol. 135(45), p. 17060-17068, or by Zhou, H. et al., in "*Angewandte Chemie International Edition*" (2011), Vol. 50(13), p. 2995-2998, or are commercially available (in particular in the case wherein $R_2$=$R_3$=hydrogen).

The N-haloimides and the aryl boron compounds having general formula (VIII) are commercially available.

As described above, said disubstituted diaryloxybenzoheterodiazole compound having general formula (I) or (II), like the disubstituted diaryloxybenzoheterodiazole compound having general formula (XII) [indicated below for greater clarity as "compound having general formula (I) or (II) or (XII)"], may advantageously be used as a spectrum converter in luminescent solar concentrators (LSCs), capable in turn of improving the performance of photovoltaic devices (or solar devices) such as, for example, photovoltaic cells (or solar cells), photovoltaic modules (or solar modules), on both rigid and flexible supports.

Said luminescent solar concentrators (LSCs) may be prepared using techniques known in the art indicated below.

As a consequence, another object of the present invention is a luminescent solar concentrator (LSC) including at least one compound having general formula (I) or (II). Compound having general formula (I) or (II) or (XII) may be used in said luminescent solar concentrator (LSC) in the following ways: dispersed in polymer, chemically bound to the polymer, in solution.

For example, the luminescent solar concentrator (LSC) may contain a transparent matrix, where the term transparent matrix means any transparent material used in the form of a support, binder, or material wherein at least one compound having general formula (I) or (II) or (XII) is dispersed or incorporated. The material used for the matrix is transparent, as such, to the radiation of interest and, in particular, to the radiation of frequency within the effective spectrum of the photovoltaic device (or solar device) such as, for example, the photovoltaic cell (or solar cell) wherein it is used. Suitable materials for the purpose of the present invention may therefore be selected from materials which are transparent to radiation of wavelengths ranging from 250 nm to 800 nm.

The transparent matrix that may be used for the purpose of the present invention may be selected, for example, from polymers. Said matrix is characterized by high transparency and high durability with respect to heat and light. Polymers that may advantageously be used for the purpose of the present invention are, for example, polymethyl methacrylate (PMMA), epoxy resins, silicone resins, polyalkylene terephthalates, polycarbonates, polystyrene, preferably polymethyl methacrylate (PMMA).

As described above, the luminescent solar concentrator (LSC) to which the present patent relates may be prepared according to known techniques such as, for example:

dispersion of said at least one compound having general formula (I) or (II) or (XII) in said at least one molten polymer [for example, molten polymethyl methacrylate (MMA)], and subsequent extrusion obtaining a coloured polymer in the form of granules which will subsequently be molded by injection or compression in order to obtain a sheet;

addition of said at least one compound having general formula (I) to a mixture comprising at least one pre-polymer [for example, a pre-polymer based on methyl methacrylate (MMA)], at least one polymerizable monomer [for example, methyl methacrylate (MMA)], at least one polymerization initiator (for example, an initiator of the free radical type), and subsequent copolymerization within a mold (a technique known as "casting") to obtain a sheet comprising at least one copolymer including said at least one polymerizable monomer and said at least one compound having general formula (I) [for example, a methyl methacrylate (MMA)/compound having general formula (I) copolymer];

addition of said at least one compound having general formula (II) or (XII) to a mixture comprising at least one pre-polymer [for example, a pre-polymer based on methyl methacrylate (MMA)], at least one polymerizable monomer [for example, methyl methacrylate (MMA)], at least one polymerization initiator (for example, an initiator of the free radical type), and subsequent copolymerization within a mold (a technique known as "casting") to obtain a sheet comprising at least one polymer based on said at least one polymerizable monomer [for example, polymethyl methacrylate (PMMA)], and at least one compound having general formula (II) or (XII) dispersed within it;

dissolution of said at least one compound having general formula (I) or (II) or (XII) and said at least one polymer [for example, polymethyl methacrylate (PMMA)], in at least one solvent obtaining a solution which is deposited on a sheet of said at least one polymer, forming a film comprising said at least one compound having general formula (I) or (II) or (XII) and said polymer, operating, for example, using a film-forming device of the "Doctor Blade" type; said solvent being then allowed to evaporate.

Alternatively, a support of the vitreous type may be used. In this respect, said at least one compound having general formula (I) or (II) or (XII) may be dissolved in at least one solvent obtaining a solution which is deposited on a sheet of said support of the vitreous type, forming a film comprising said at least one compound having general formula (I) or (II) or (XII), operating, for example, using a film-forming device of the "Doctor Blade" type; said solvent being then allowed to evaporate.

Yet a further object of the present invention is a photovoltaic device (or solar device) comprising at least one photovoltaic cell (or solar cell), and at least one luminescent solar concentrator (LSC) including at least one compound having general formula (I) or (II).

Said photovoltaic device (or solar device) may be obtained, for example, by assembling the aforesaid luminescent solar concentrator with a photovoltaic cell (or solar cell).

In accordance with a preferred embodiment of the present invention, the aforesaid solar concentrator may be made in the form of a transparent sheet obtained by dissolving said at least one compound having general formula (I) or (II) or (XII) and the polymer used for the purpose in at least one solvent obtaining a solution which is deposited on a sheet of said polymer, forming a film comprising said at least one compound having general formula (I) or (II) or (XII) and said polymer, operating, for example, using a film-forming device of the "Doctor Blade" type; said solvent being then allowed to evaporate. In said photovoltaic devices (or solar devices), said sheets may then be coupled with a photovoltaic cell (or solar cell).

Figure 1:
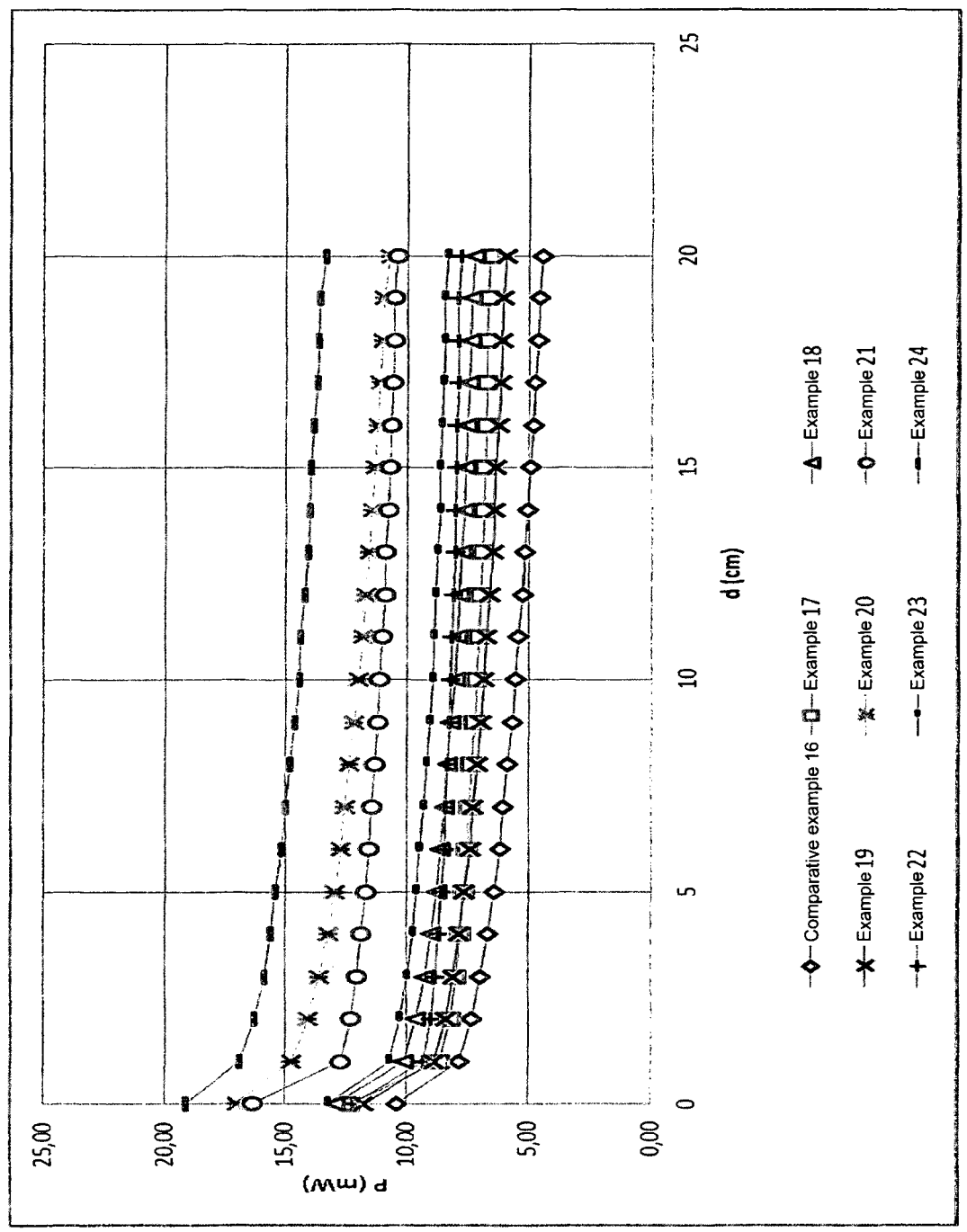
FIG. 1 shows the graph for the value of the power (P) generated expressed in mW (shown as the ordinate) as a function of the distance (d) from the edge to which the photovoltaic cell was attached, expressed in cm (shown as the abscissa).
Figure 2:
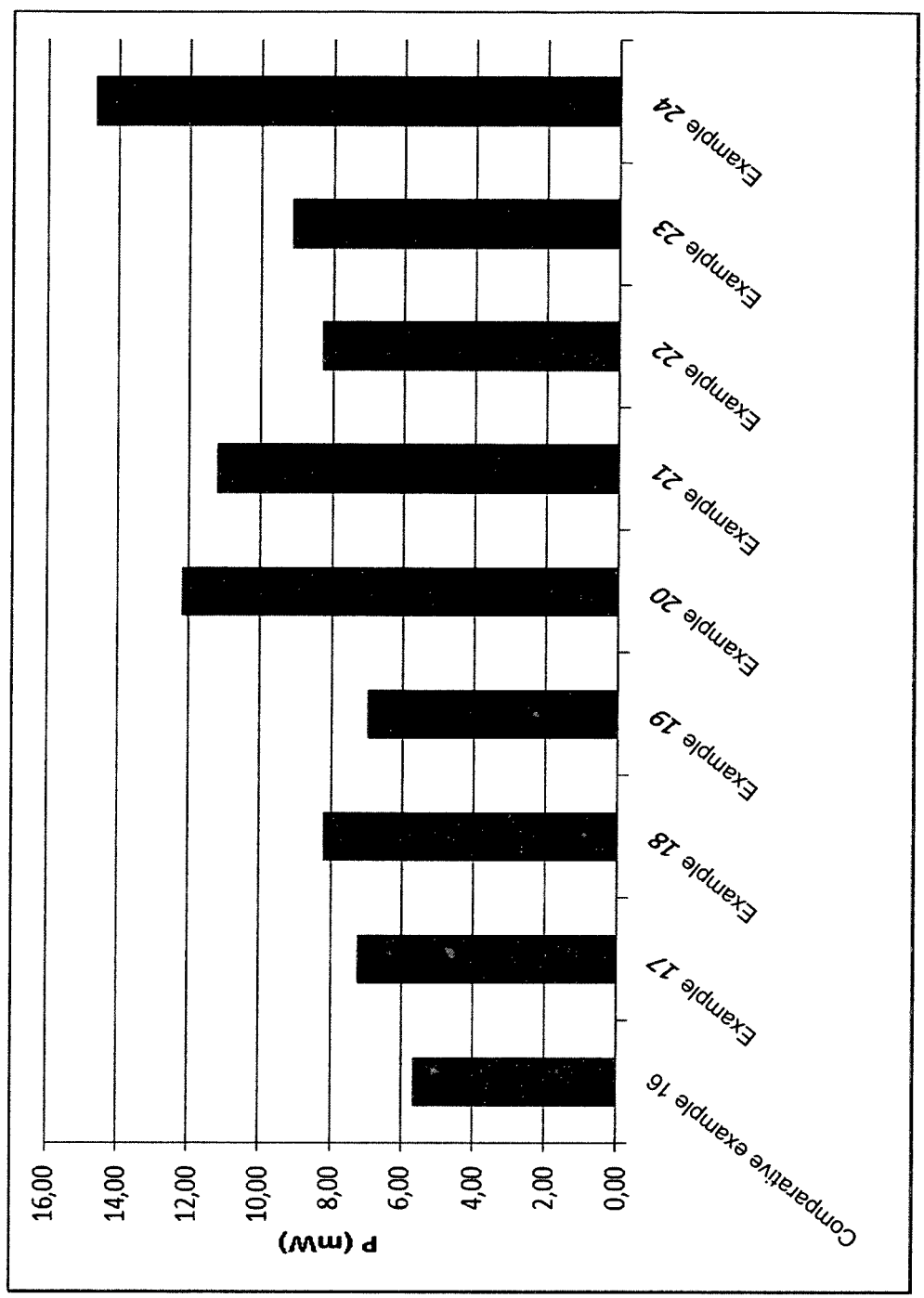
FIG. 2 shows the value of the power (P) generated expressed in mW (shown as the ordinate) obtained (the example number is shown as the abscissa).

For a better understanding of the present invention and in order to put it into practice, a number of illustrative and non-limiting examples are described below. 4,7-di-(thien-2'-yl)-2,1,3-benzothiadiazole (DTB) was obtained as described in Example 1 of international patent application WO 2012/007834 in the name of Applicant, the contents of which are incorporated herein as a reference.

EXAMPLE 1

Synthesis of methyl 4-(6-phenoxy-4,7-di(2-thienyl) benzo[3,4-c]1,2,5-thiadiazo-5-yloxy)benzoate Having Formula (IIa)

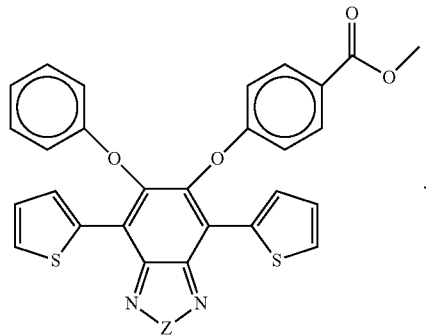

(IIa)

Methyl 4-hydroxybenzoate (Aldrich) (453 mg; 3 mmoles) and potassium carbonate (Aldrich) (1 g; 7.2 mmoles) were added to a suspension of 5,6-difluoro-4,7-bis(2-thienyl)-2,1,3-benzothiadiazole (Sunatech) (1 g; 3 mmoles) in N,N-dimethylformamide (Aldrich) (12 ml) in a 100 ml flask equipped with a magnetic stirrer, thermometer and condenser, under an inert atmosphere: the reaction mixture obtained was heated to 100° C. and held at said temperature, under stirring, for 5 hours, at the end of which phenol (Aldrich) (564 mg; 6 mmoles) was added and the whole was held under stirring, at 92° C., for 12 hours. Subsequently, after cooling to ambient temperature (25° C.), distilled water (30 ml) was added to the reaction mixture obtained and the whole was extracted with dichloromethane (Aldrich) (3×50 ml). The organic phase obtained was washed to neutral with distilled water (3×25 ml) and subsequently dried on sodium sulfate (Aldrich). Residual solvent was removed by distillation under reduced pressure. The residue obtained was purified by elution on a silica gel chromatography column [eluent: in a gradient from n-heptane (Aldrich)/dichloromethane (Aldrich) in a ratio of 9/1 (v/v) to r-heptane (Aldrich)/dichloromethane (Aldrich)/ethyl acetate (Aldrich) in a ratio of 8/1.5/0.5 (v/v/v)], obtaining 1.5 g of methyl 4-(6-phenoxy-4,7-di(2-thienyl)benzo[3,4-c]1,2,5-thiadiazo-5-yloxy)benzoate having formula (IIa) (yield=92%).

EXAMPLE 2

Synthesis of methyl 4-{6-[4-(methoxycarbonyl) phenoxy]-4,7-di(2-thienyl) benzo[3,4-c]1,2,5-thiadiazo-5-yloxy}benzoate Having Formula (IIb)

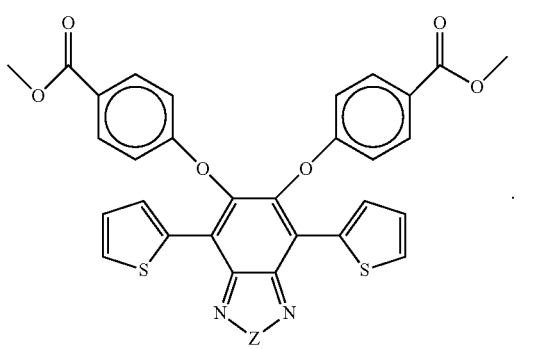

(IIb)

Methyl 4-hydroxybenzoate (Aldrich) (882 mg; 5.8 mmoles) and potassium carbonate (Aldrich) (952 mg; 6.9 mmoles) were added to a suspension of 5,6-difluoro-4,7-bis (2-thienyl)-2,1,3-benzothiadiazole (Sunatech) (928 mg; 2.8 mmoles) in N,N-dimethylformamide (Aldrich) (12 ml) in a 100 ml flask equipped with a magnetic stirrer, thermometer and condenser, under an inert atmosphere: the reaction mixture obtained was heated to 92° C. and held at said temperature, under stirring, for 12 hours.

Subsequently, after the addition of 20 ml of distilled water, there was obtained a precipitate which was recovered by filtration and washed with distilled water (30 ml) obtaining 1.6 g of methyl 4-{6-[4-(methoxycarbonyl)phenoxy]-4,7-di(2-thienyl)benzo[3,4-c]1,2,5-thiadiazo-5-yloxy}benzoate having formula (IIb) (yield=95%).

EXAMPLE 3

Synthesis of methyl 4-[4,7-bis(5-bromo(2-thienyl))-6-phenoxybenzo[3,4-c]1,2,5-thiadiazo-5-yloxy]benzoate Having Formula (a)

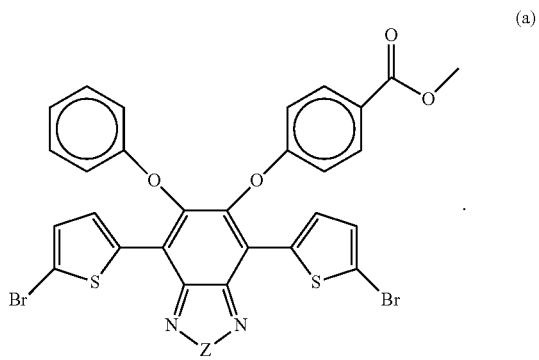

(a)

N-bromosuccinimide (Aldrich) (566.4 mg; 3.2 mmoles) was added to a suspension of methyl 4-(6-phenoxy-4,7-di (2-thienyl)benzo[3,4-c]1,2,5-thiadiazo-5-yloxy)benzoate having formula (IIa) obtained as described in Example 1 (800 mg; 1.5 mmoles) in tetrahydrofuran (Aldrich) (8.3 ml) in a 100 ml flask equipped with a magnetic stirrer, thermometer and condenser, under an inert atmosphere. the reaction mixture obtained was left in the dark, under stirring, at ambient temperature (25° C.) for 12 hours. Subsequently, after the addition of 20 ml of distilled water, a precipitate was obtained which was recovered by filtration and washed with distilled water (30 ml), obtaining 945 mg of methyl 4-[4,7-bis(5-bromo(2-thienyl))-6-phenoxybenzo[3,4-c]1,2,5-thiadiazo-5-yloxy]benzoate having formula (a) (yield=90%).

EXAMPLE 4

Synthesis of methyl 4-{4,7-bis[5-(2,5-dimethylphenyl)(2-thienyl)]-6-phenoxy benzo[3,4-c]1,2,5-thiadiazo-5-yloxy}benzoate Having Formula (IIc)

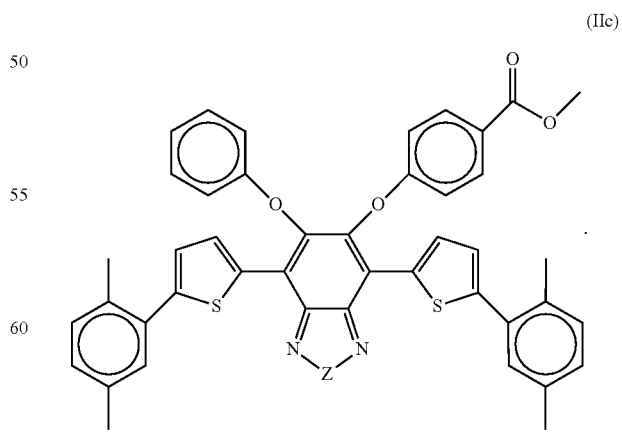

(IIc)

2,5-dimethylphenylboronic acid (Aldrich) (510 mg; 3.4 mmoles) and a 2.17 M aqueous solution of potassium carbonate (Aldrich) (1.4 g in 4.8 ml of water; 10.4 mmoles) were added to a solution of methyl 4-[4,7-bis(5-bromo(2-thienyl))-6-phenoxybenzo[3,4-c]1,2,5-thiadiazo-5-yloxy]benzoate (a) obtained as described in Example 3 (900 mg; 1.3 mmoles) in 1,4-dioxane (Aldrich) (30 ml) in a 100 ml flask equipped with a magnetic stirrer, thermometer and condenser, under an inert atmosphere. After the air present had been removed by means of three vacuum/nitrogen cycles, palladium-tetrakistriphenylphosphine (Aldrich) (75.0 mg; 0.065 mmoles) was added, obtaining a reaction mixture which was heated to 95° C. and held at said temperature, under stirring, for 14 hours. Subsequently, the reaction mixture was poured into distilled water (50 ml) and extracted with dichloromethane (Aldrich) (3×25 ml). The organic phase obtained was washed to neutral with distilled water (3×25 ml), and subsequently dried on sodium sulfate (Aldrich). Residual solvent was removed by distillation under reduced pressure. The residue obtained was purified by elution on a silica gel chromatography column [eluent: n-heptane (Aldrich)/dichloromethane (Aldrich) mixture in a ratio of 9/1 (v/v)], obtaining 828.7 mg of methyl-4-{4,7-bis[5-(2,5-dimethylphenyl)(2-thienyl)]-6-phenoxy benzo[3,4-c]1,2,5-thiadiazo-5-yloxy}benzoate having formula (IIc) (yield=85%).

EXAMPLE 5

Synthesis of methyl 4-{4,7-bis[5-(2,6-dimethylphenyl)(2-thienyl)]-6-phenoxy benzo[3,4-c]1,2,5-thiadiazo-5-yloxy}benzoate Having Formula (IId)

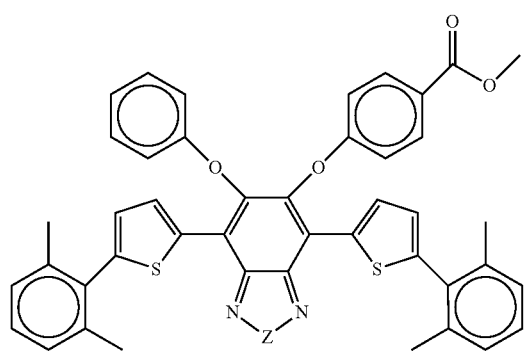

(IId)

2,6-dimethylphenylboronic acid (Aldrich) (510 mg; 3.4 mmoles) and a 2.17 M aqueous solution of potassium carbonate (Aldrich) (1.4 g in 4.8 ml of water; 10.4 mmoles) were added to a solution of methyl 4-[4,7-bis(5-bromo(2-thienyl))-6-phenoxybenzo[3,4-c]1,2,5-thiadiazo-5-yloxy]benzoate obtained as described in Example 3 (900.0 mg; 1.3 mmoles) in 1,4-dioxane (Aldrich) (30 ml) in a 100 ml flask equipped with a magnetic stirrer, thermometer and condenser, under an inert atmosphere. After the air present had been removed by means of three vacuum/nitrogen cycles, palladium-tetrakistriphenylphosphine (Aldrich) (75.0 mg; 0.065 mmoles) was added, obtaining a reaction mixture which was heated to 95° C. and held at said temperature, under stirring, for 14 hours. Subsequently, the reaction mixture was poured into distilled water (50 ml) and extracted with dichloromethane (Aldrich) (3×25 ml). The organic phase obtained was washed to neutral with distilled water (3×25 ml), and subsequently dried on sodium sulfate (Aldrich). Residual solvent was removed by distillation under reduced pressure. The residue obtained was purified by elution on a silica gel chromatography column [eluent: n-heptane (Aldrich)/dichloromethane (Aldrich) mixture in a ratio of 9/1 (v/v)], obtaining 828.7 mg of methyl-4-{4,7-bis[5-(2,6-dimethylphenyl)(2-thienyl)]-6-phenoxy benzo[3,4-c]1,2,5-thiadiazo-5-yloxy}benzoate having formula (IId) (yield=85%).

EXAMPLE 6

Synthesis of methyl 4-{4,7-bis(5-bromo(2-thienyl))-6-[4-(methoxycarbonyl) phenoxy]-benzo[3,4-c]1,2,5-thiadiazo-5-yloxy}benzoate Having Formula (b)

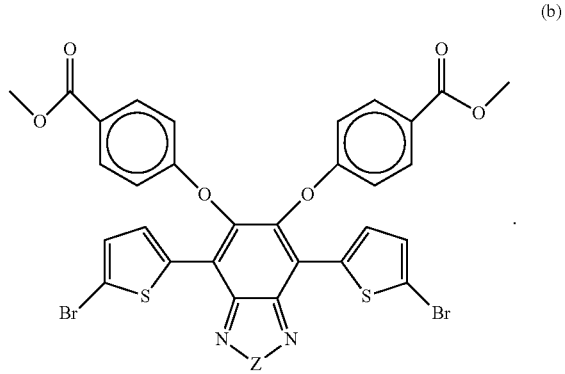

(b)

N-bromosuccinimide (Aldrich) (478 mg; 2.7 mmoles) was added to a suspension of methyl 4-(6-[4-(methoxycarbonyl)phenoxy]-4,7-di(2-thienyl)benzo[3,4-c]1,2,5-thiadiazo-5-yloxy}benzoate obtained as described in Example 2 (720 mg; 1.2 mmoles) in tetrahydrofuran (Aldrich) (18 ml) in a 100 ml flask equipped with a magnetic stirrer, under an inert atmosphere: the reaction mixture obtained was left in the dark, under stirring, at ambient temperature (25° C.), for 12 hours. Subsequently, after the addition of 20 ml of distilled water, there was obtained a precipitate which was recovered by filtration and washed with distilled water (30 ml), obtaining 773 mg of methyl 4-{4,7-bis(5-bromo(2-thienyl))-6-[4-(methoxycarbonyl)phenoxy]benzo[3,4-c]1,2,5-thiadiazo-5-yloxy}benzoate having formula (b) (yield=85%).

EXAMPLE 7

Synthesis of methyl 4-{4,7-bis[5-(2,6-dimethylphenyl)(2-thienyl)]-6-[4-(methoxy carbonyl)phenoxy]benzo[3,4-c]1,2,5-thiadiazo-5-yloxy}benzoate Having Formula (IIe)

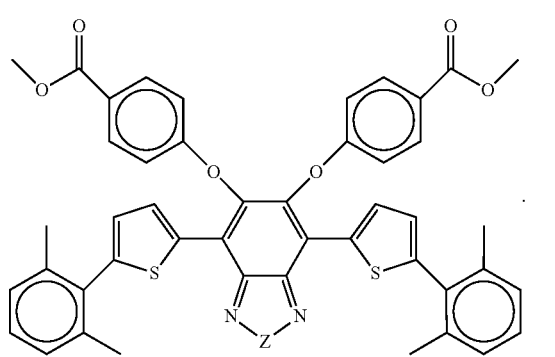

(IIe)

2,6-di-methylphenylboronic acid (Aldrich) (373.7 mg; 2.5 mmoles) and a 2.1 M aqueous solution of potassium carbonate (Aldrich) (1 g; 7.2 mmoles) were added to a solution of methyl 4-{4,7-bis(5-bromo(2-thienyl))-6-[4-(methoxycarbonyl)phenoxy]benzo[3,4-c]1,2,5-thiadiazo-5-yloxy}-benzoate obtained as described in Example 6 (700 mg; 0.92 mmoles) in 1,4-dioxane (Aldrich) (20 ml) in a 100 ml flask equipped with a magnetic stirrer, thermometer and condenser, under an inert atmosphere. After the air present had been removed by means of three vacuum/nitrogen cycles, palladium tetrakis(triphenylphosphine) (Aldrich) (47.9 mg; 0.041 mmoles) was added, obtaining a reaction mixture which was heated to 85° C. and held at said temperature, under stirring, for 14 hours. Subsequently, the reaction mixture was poured into distilled water (50 ml) and extracted with dichloromethane (Aldrich) (3×25 ml). The organic phase obtained was washed to neutral with distilled water (3×25 ml), and subsequently dried on sodium sulfate (Aldrich). Residual solvent was removed by distillation under reduced pressure. The residue obtained was purified by elution on a silica gel chromatography column [eluent: n-heptane (Aldrich)/dichloromethane (Aldrich) mixture in a ratio of 9/1 (v/v)], obtaining 594.7 mg of methyl 4-{4,7-bis[5-(2,6-dimethylphenyl)(2-thienyl)]-6-[4-(methoxy carbonyl)phenoxy]benzo[3,4-c]1,2,5-thiadiazo-5-yloxy}benzoate having formula (IIe) (yield=80%).

EXAMPLE 8

Synthesis of 4-(6-phenoxy-4,7-di(2-thienyl)benzo[3,4-c]1,2,5-thiadiazo-5-yloxy) benzoic Acid Having Formula (c)

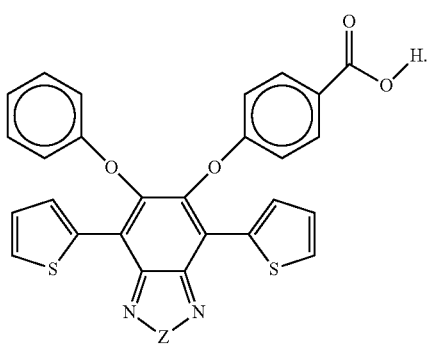

(c)

Sodium hydroxide (Aldrich) (1.1 g; 28.0 mmoles) was added to a suspension of methyl 4-(6-phenoxy-4,7-di(2-thienyl)benzo[3,4-c]1,2,5-thiadiazo-5-yloxy)benzoate having formula (IIa) obtained as described in Example 1 (1.5 g; 2.8 mmoles) in ethanol (Aldrich) (50 ml) in a 100 ml flask equipped with a magnetic stirrer, thermometer and condenser, under an inert atmosphere. The reaction mixture was heated to 80° C. and held at said temperature, under stirring, for 5 hours. Subsequently, the reaction mixture was poured into distilled water (50 ml) and extracted with dichloromethane (Aldrich) (50 ml). The aqueous phase obtained was acidified to pH 1 through the addition of a 0.1M solution of hydrochloric acid (Aldrich) and extracted with dichloromethane (3×50 ml). The organic phase obtained was washed with brine and subsequently dried on sodium sulfate. Residual solvent was removed by distillation under reduced pressure obtaining 1.4 g of 4-(6-phenoxy-4,7-di(2-thienyl)benzo[3,4-c]1,2,5-thiadiazo-5-yloxy)benzoic acid having formula (c) (yield=95%).

EXAMPLE 9

Synthesis of 2-[4-(6-phenoxy-4,7-di(2-thienyl)benzo[3,4-c]1,2,5-thiadiazo-5-yloxy)phenylcarbonyloxy]ethyl-2-methylprop-2-enoate Having Formula (Ia)

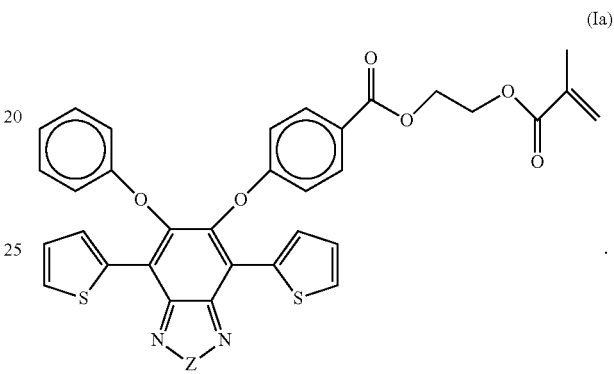

(Ia)

2-hydroxyethyl methacrylate (HEMA) (Aldrich) (370.5 mg; 2.85 mmoles) and 4-(N,N-dimethylamino)pyridine (46.4 mg; 0.38 mmoles) were added to a suspension of 4-(6-phenoxy-4,7-di(2-thienyl)benzo[3,4-c]1,2,5-thiadiazo-5-yloxy)benzoic acid obtained as described in Example 8 (501.6 mg; 0.95 mmoles) in anhydrous dichloromethane (Aldrich) (17 ml) in a 100 ml flask equipped with a magnetic stirrer, under an inert atmosphere. A 0.35 M solution of 1-ethyl-[3-(3-dimethylamino)propyl]carbodiimide hydrochloride (WSC) (Aldrich) in anhydrous dichloromethane [236.7 mg; 1.2 mmoles in 3.4 ml of anhydrous dichloromethane (Aldrich)] was added dropwise to the suspension so obtained, at 0° C., under stirring, over 30 minutes. After 15 minutes, under stirring, at said temperature, the reaction mixture was heated to 20° C. and left at said temperature, under stirring, for 12 hours. Subsequently, the reaction mixture was poured into water (25 ml) and extracted with dichloromethane (Aldrich) (3×50 ml). The organic phase obtained was washed to neutral first with a 0.1 M aqueous solution of hydrochloric acid (Aldrich) (20 ml), then with a saturated aqueous solution of sodium bicarbonate (Aldrich) (30 ml) and finally with brine, and subsequently dried on sodium sulfate. Residual solvent was removed by distillation under reduced pressure. The residue obtained was purified by elution on a neutral alumina column [eluent in a gradient from n-heptane (Aldrich)/dichloromethane (Aldrich) in a ratio of 9/1 (v/v) to n-heptane (Aldrich)/dichloromethane (Aldrich)/ethyl acetate (Aldrich) in a ratio of 8.5/1/0.5 (v/v/v)], obtaining 500 mg of 2-[4-(6-phenoxy-47-di(2-thienyl)benzo[3,4-c]1,2,5-thiadiazo-5-yloxy)phenylcarbonyloxy]ethyl-2-methyl-prop-2-enoate having formula (Ia) (yield=82%).

EXAMPLE 10

Synthesis of 4-[6-(4-carboxyphenoxy)-4,7-di(2-thienyl)benzo[c]1,2,5-thiadiazo-5-yloxy]benzoic Acid Having Formula (d)

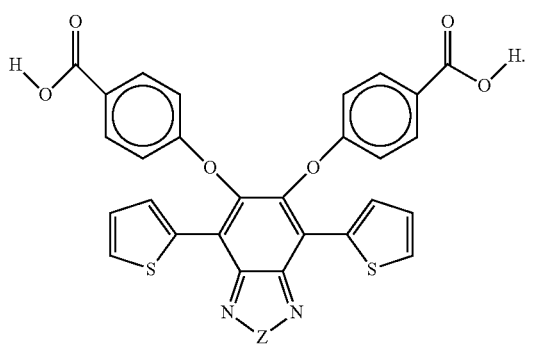

Sodium hydroxide (Aldrich) (2 g; 50 mmoles) was added to a suspension of methyl 4-{6-[4-(methoxycarbonyl)phenoxy]-4,7-di(2-thienyl)benzo[3,4-c]1,2,5-thiadiazo-5-yloxy}-benzoate having formula (IIb) obtained as described in Example 2 (1.5 g; 2.5 mmoles) in ethanol (Aldrich) (83 ml) in a 100 ml flask equipped with a magnetic stirrer, thermometer and condenser, under an inert atmosphere. The reaction mixture was heated to 80° C. and held at said temperature, under stirring, for 5 hours. Subsequently, the reaction mixture was poured into distilled water (50 ml) and extracted with dichloromethane (Aldrich) (1×50 ml). The aqueous phase obtained was acidified to pH 1 through the addition of a 0.1M solution of hydrochloric acid (Aldrich) and extracted with dichloromethane (3×50 ml). The organic phase obtained was washed with brine and subsequently dried on sodium sulfate. Residual solvent was removed by distillation under reduced pressure obtaining 1.3 g of 4-[6-(4-carboxyphenoxy)-4,7-di(2-thienyl)benzo[c]1,2,5-thiadiazo-5-yloxy]benzoic acid having formula (d) (yield=91%).

EXAMPLE 11

Synthesis of 2-{4-[6-(4-{[2-(2-methylprop-2-enoyloxy)ethyl]oxycarbonyl} phenoxy)-4,7-di(2-thienyl)benzo[3,4-c]1,2,5-thiadiazo-5-yloxy]phenyl carbonyloxy}ethyl 2-methyl-prop-2-enoate Having Formula (Ib)

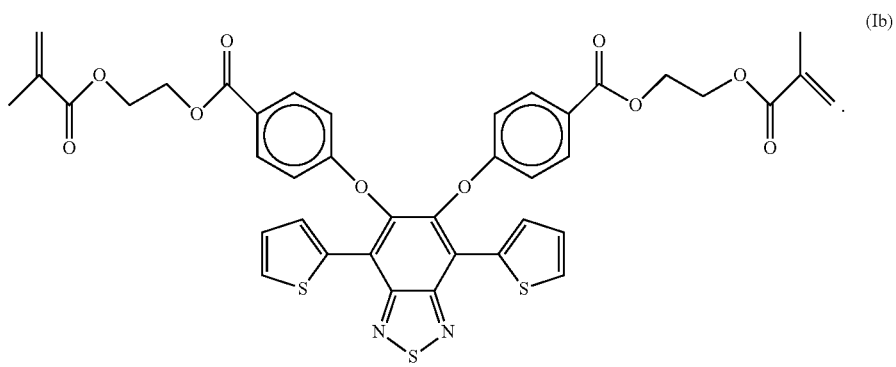

2-hydroxyethyl methacrylate (HEMA) (Aldrich) (741 mg; 5.7 mmoles) and 4-(N,N-dimethylamino)pyridine (92.7 mg; 0.76 mmoles) were added to a suspension of 4-[6-(4-carboxyphenoxy)-4,7-di(2-thienyl)benzo[c]1,2,5-thiadiazo-5-yloxy]benzoic acid obtained as described in Example 8 (543.4 mg; 0.95 mmoles) in anhydrous dichloromethane (Aldrich) (34 ml) in a 100 ml flask equipped with a magnetic stirrer, under an inert atmosphere. A 0.32 M solution of 1-ethyl-[3-(3-dimethylamino)propyl]-carbodiimide hydrochloride (WSC) (Aldrich) in anhydrous dichloromethane [473.5 mg; 2.5 mmoles in 7.8 ml of anhydrous dichloromethane (Aldrich)] was added dropwise to the suspension so obtained, at 0° C., under stirring, over 30 minutes. After 15 minutes under stirring at said temperature, the reaction mixture was heated to 20° C. and left at said temperature, under stirring, for 12 hours. Subsequently, the reaction mixture was poured into water (50 ml) and extracted with dichloromethane (Aldrich) (3×50 ml). The organic phase obtained was washed to neutral first with a 0.1 M aqueous solution of hydrochloric acid (Aldrich) (30 ml), then with a saturated aqueous solution of sodium bicarbonate (Aldrich) (40 ml) and finally with brine, and subsequently dried on sodium sulfate. Residual solvent was removed by distillation under reduced pressure. The residue obtained was purified by elution on a neutral alumina column [eluent n-heptane (Aldrich)/dichloromethane (Aldrich)/ethyl acetate (Aldrich) in a ratio of 8/1/1 (v/v/v)], obtaining 541.3 mg of 2-{4-[6-(4-{[2-(2-methylprop-2-enoyloxy)ethyl]oxycarbonyl}phenoxy)-4,7-di(2-thienyl)benzo[3,4-c]1,2,5-thiadiazo-5-yloxy]phenylcarbonyloxy}ethyl 2-methylprop-2-enoate (having formula (Ib) (yield=72%).

EXAMPLE 12

Synthesis of 4-{4,7-bis[5-(2,5-dimethylphenyl)(2-thienyl)]-6-phenoxybenzo[3,4-c]1,2,5-thiadiazo-5-yloxy}benzoic Acid Having Formula (e)

(e)

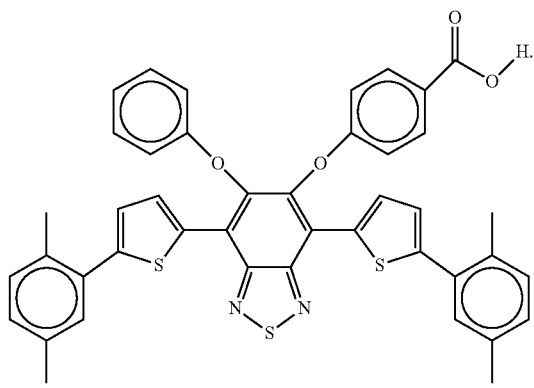

Sodium hydroxide (Aldrich) (440 mg; 11 mmoles) was added to a suspension of methyl 4-{4,7-bis[5-(2,5-dimethylphenyl)(2-thienyl)]-6-phenoxybenzo[3,4-c]1,2,5-thiadiazo-5-yloxy}benzoate (6) obtained as described in Example 5 (825 mg; 1.1 mmoles) in ethanol (Aldrich) (25 ml) in a 100 ml flask equipped with a magnetic stirrer, thermometer and condenser, under an inert atmosphere. The reaction mixture was heated to 80° C. and held at said temperature, under stirring, for 5 hours. Subsequently, the reaction mixture was poured into distilled water (50 ml) and extracted with dichloromethane (Aldrich) (1×50 ml). The aqueous phase obtained was acidified to pH 1 through the addition of a 0.1M solution of hydrochloric acid (Aldrich) and extracted with dichloromethane (3×50 ml). The organic phase obtained was washed with brine and subsequently dried on sodium sulfate. Residual solvent was removed by distillation under reduced pressure obtaining 730 mg of 4-{4,7-bis[5-(2,5-dimethylphenyl)(2-thienyl)]-6-phenoxybenzo[3,4-c]1,2,5-thiadiazo-5-yloxy}benzoic acid having formula (e) (yield=90%).

EXAMPLE 13

Synthesis of 2-(4-{4,7-bis[5-(2,5-dimethylphenyl)(2-thienyl)]-8-phenoxybenzo [3,4-c]1,2,5-thiadiazo-5-yloxy}phenylcarbonyloxy)ethyl-2-methylprop-2-enoate having formula (Ic)

(Ic)

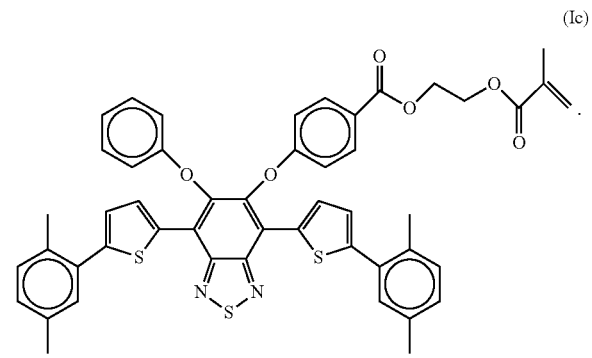

2-hydroxyethyl methacrylate (HEMA) (Aldrich) (370 mg; 2.85 mmoles) and 4-(N,N-dimethylamino)pyridine (46.4 mg; 0.38 mmoles) were added to a suspension of 4-{4,7-bis[5-(2,5-dimethylphenyl)(2-thienyl)]-6-phenoxybenzo [3,4-c]1,2,5-thiadiazo-5-yloxy}benzoic acid obtained as described in Example 12 (700 mg; 0.95 mmoles) in anhydrous dichloromethane (Aldrich) (17 ml) in a 100 ml flask equipped with a magnetic stirrer, under an inert atmosphere. A 0.35 M solution of 1-ethyl-[3-(3-dimethylamino)propyl]-carbodiimide hydrochloride (WSC) (Aldrich) in anhydrous dichloromethane [236.7 mg; 1.2 mmoles in 3.4 ml of anhydrous dichloromethane (Aldrich)] was added dropwise to the suspension so obtained, at 0° C., under stirring, over 30 minutes. After 15 minutes under stirring at said temperature, the reaction mixture was heated to 20° C. and left at said temperature, under stirring, for 12 hours. Subsequently, the reaction mixture was poured into water (25 ml) and extracted with dichloromethane (Aldrich) (3×50 ml). The organic phase obtained was washed to neutral first with a 0.1 M aqueous solution of hydrochloric acid (Aldrich) (20 ml), then with a saturated aqueous solution of sodium bicarbonate (Aldrich) (30 ml) and finally with brine, and subsequently dried on sodium sulfate. Residual solvent was removed by distillation under reduced pressure. The residue obtained was purified by elution on a neutral alumina column [eluent in a gradient from n-heptane (Aldrich)/dichloromethane (Aldrich) in a ratio of 9/1 (v/v) to n-heptane (Aldrich)/dichloromethane (Aldrich)/ethyl acetate (Aldrich) in a ratio of 8.5/1/0.5 (v/v/v)], obtaining 644 mg of 2-(4-{4,7-bis[5-(2,5-dimethylphenyl)(2-thienyl)]-6-phenoxybenzo[3,4-c]1,2,5-thiadiazo-5- yloxy}phenylcarbonyloxy) ethyl-2-methylprop-2-enoate having formula (Ic) (yield=80%).

EXAMPLE 14

Synthesis of 5-(4-methoxyphenoxy)-6-phenoxy-4,7-di(2-thienyl)benzo[c]1,2,5-thiadiazole Having Formula (XIIIa)

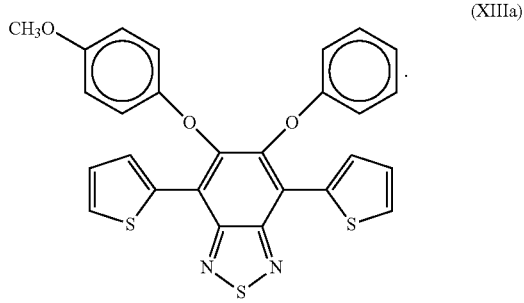

4-methoxyphenol (Aldrich) (314 mg; 2.5 mmoles) and potassium carbonate (Aldrich) (873 mg; 6.3 mmoles) were added to a suspension of 5,6-difluoro-4,7-bis(2-thienyl)-2,1,3-benzothiadiazole (Sunatech) (851 mg; 2.5 mmoles) in N,N-dimethylformamide (Aldrich) (9 ml) in a 100 ml flask equipped with a magnetic stirrer, thermometer and condenser, under an inert atmosphere: the reaction mixture obtained was heated to 95° C. and held at said temperature, under stirring, for 4 hours, at the end of which there was added phenol (Aldrich) (387 mg; 4.1 mmoles) and the whole was held under stirring, at 92° C., for 12 hours. Subsequently, after cooling to ambient temperature (25° C.), distilled water (30 ml) was added to the reaction mixture obtained and the whole was extracted with dichloromethane (Aldrich) (3×50 ml). The organic phase obtained was washed to neutral with distilled water (3×25 ml) and subsequently dried on sodium sulfate (Aldrich).

Residual solvent was removed by distillation under reduced pressure. The residue obtained was purified by elution on a silica gel chromatography column [eluent: in a gradient from n-heptane (Aldrich)/dichloromethane (Aldrich) in a ratio of 9.5/0.5 (v/v) to n-heptane (Aldrich)/dichloromethane (Aldrich) in a ratio of 9/1 (v/v)], obtaining 1.2 g of methyl 4-(6-phenoxy-4,7-di(2-thienyl)benzo[3,4-c]1,2,5-thiadiazo-5-yloxy) benzoate having formula (XIIIa) (yield=93%).

EXAMPLE 15

Synthesis of 4-(6-phenoxy-4,7-di(2-thienyl)benzo[3,4-c]1,2,5-thiadiazo-5-yloxy) benzenecarbonitrile Having Formula (XIIIb)

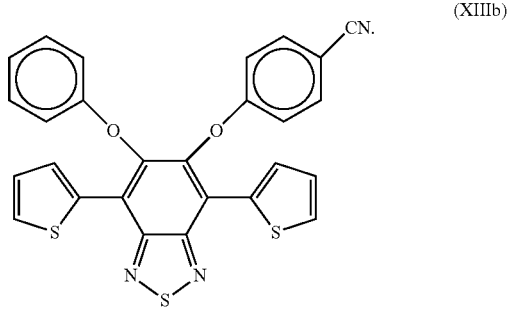

4-hydroxybenzonitrile (Aldrich) (143 mg; 1.2 mmoles) and potassium carbonate (Aldrich) (414 mg; 3 mmoles) were added to a suspension of 5,6-difluoro-4,7-bis(2-thienyl)-2,1,3-benzothiadiazole (Sunatech) (400 mg; 1.2 mmoles) in N,N-dimethylformamide (Aldrich) (5 ml) in a 100 ml flask equipped with a magnetic stirrer, thermometer and condenser, under an inert atmosphere: the reaction mixture obtained was heated to 100° C. and held at said temperature, under stirring, for 5 hours, at the end of which phenol (Aldrich) (188 mg; 2 mmoles) was added and the whole was held under stirring, at 92° C., for 12 hours. Subsequently, after cooling to ambient temperature (25° C.), distilled water (30 ml) was added to the reaction mixture obtained and the whole was extracted with dichloromethane (Aldrich) (3×50 ml). The organic phase obtained was washed to neutral with distilled water (3×25 ml) and subsequently dried on sodium sulfate (Aldrich). Residual solvent was removed by distillation under reduced pressure. The residue obtained was purified by elution on a silica gel chromatography column [eluent: in a gradient from n-heptane (Aldrich)/dichloromethane (Aldrich) in a ratio of 9/1 (v/v) to r-heptane (Aldrich)/dichloromethane (Aldrich)/ethyl acetate in a ratio of 8/1.5/0.5 (v/v/v)], obtaining 560 mg of 4-(6-phenoxy-4,7-di(2-thienyl)benzo[3,4-c]1,2,5-thiadiazo-5-yloxy)benzenecarbonitrile having formula (XIIIb) (yield=92%).

EXAMPLE 16 (COMPARATIVE)

6 g of Altuglas VSUVT 100 polymethyl methacrylate (PMMA) and 49.5 mg of 4,7-di-(thien-2'-yl)-2,1,3-benzothiadiazole (DTB), were dissolved in 30 ml of 1,2-dichlorobenzene (Aldrich). The solution obtained was subsequently deposited uniformly on a sheet of polymethyl methacrylate (dimensions 300 mm×90 mm×6 mm) using a film-forming device of the "Doctor Blade" type and the solvent was allowed to evaporate off at ambient temperature (25° C.), in a gentle flow of air, for 24 hours. From this there resulted a transparent sheet of a yellow color imparted by the film, the thickness of which was ranging from 100 μm to 50 μm.

An IXYS-KXOB22-12 photovoltaic cell having a surface area of 1.2 cm$^2$ was then applied to one of the edges of the polymer sheet.

The main surface of the polymer sheet [that coated with the thin film containing 4,7-di-(thien-2'-yl)-2,1,3-benzothiadiazole (DTB)] was then illuminated with a light source of power 1 sun (1000 W/m$^2$) and the electrical power generated through the effect of the illumination was measured.

The power (P) measurements have been realized by illuminating a portion of sheet of dimensions 100 mm×90 mm, at an increasing distance (d) from the edge to which the photovoltaic cell was attached. These measurements at a variable distance from the photovoltaic cell allow the quantification of the contribution of wave guide, edge and autoabsorption effects.

It will be seen that, in the absence of edge effects, the mean power generated was 5.69 mW (FIG. 1).

EXAMPLE 17

6 g of Altuglas VSUVT 100 polymethyl methacrylate (PMMA) and 107.8 mg of methyl 4-{6-[4-(methoxycarbonyl)phenoxy]-4,7-di(2-thienyl) benzo[3,4-c]1,2,5-thiadiazo-5-yloxy}benzoate having formula (IIb) obtained as described in Example 2, were dissolved in 30 ml of 1,2-dichlorobenzene (Aldrich). The solution obtained was then uniformly deposited on a sheet of polymethyl methacrylate (dimensions 300 mm×90 mm×6 mm) using a film-forming device of the "Doctor Blade" type and the solvent was allowed to evaporate off at ambient temperature (25° C.), in a gentle flow of air, for 24 hours. From this there resulted a transparent sheet of a red color imparted by the film, the thickness of which was ranging from 100 µm to 50 µm.

An IXYS-KXOB22-12 photovoltaic cell having a surface area of 1.2 cm$^2$ was then applied to one of the edges of the polymer sheet The main surface of the polymer sheet (that coated with the thin film) was then illuminated with a light source of power 1 sun (1000 W/m$^2$) and the electrical power generated through the effect of the illumination was measured.

The power (P) measurements have been realized by illuminating a portion of sheet of dimensions 100 mm×90 mm, at an increasing distance (d) from the edge to which the photovoltaic cell was attached. These measurements at a variable distance from the photovoltaic cell allow the quantification of the contribution of wave guide, edge and autoabsorption effects.

It will be seen that, in the absence of edge effects, the mean power generated was 7.25 mW (FIG. 1).

EXAMPLE 18

6 g of Altuglas VSUVT 100 polymethyl methacrylate (PMMA) and 92.6 mg of 5-(4-methoxyphenoxy)-6-phenoxy-4,7-di(2-thienyl)benzo[c]1,2,5-thiadiazole having formula (XIIIa) obtained as described in Example 14, were dissolved in 30 ml of 1,2-dichlorobenzene (Aldrich). The solution obtained was then uniformly deposited on a sheet of polymethyl methacrylate (dimensions 300 mm×90 mm×6 mm) using a film-forming device of the "Doctor Blade" type and the solvent was allowed to evaporate off at ambient temperature (25° C.), in a gentle flow of air, for 24 hours. From this there resulted a transparent sheet of a red color imparted by the film, the thickness of which was ranging from 100 µm to 50 µm.

An IXYS-KXOB22-12 photovoltaic cell having a surface area of 1.2 cm$^2$ was then applied to one of the edges of the polymer sheet.

The main surface of the polymer sheet (that coated with the thin film) was then illuminated with a light source of power 1 sun (1000 W/m$^2$) and the electrical power generated through the effect of the illumination was measured The power (P) measurements have been realized by illuminating a portion of sheet of dimensions 100 mm×90 mm, at an increasing distance (d) from the edge to which the photovoltaic cell was attached. These measurements at a variable distance from the photovoltaic cell allow the quantification of the contribution of wave guide, edge and autoabsorption effects.

It will be seen that, in the absence of edge effects, the mean power generated was 8.21 mW (FIG. 1).

EXAMPLE 19

6 g of Altuglas VSUVT 100 polymethyl methacrylate (PMMA) and 91.7 mg of 4-(6-phenoxy-4,7-di(2-thienyl) benzo[3,4-c]1,2,5-thiadiazo-5-yloxy) benzenecarbonitrile having formula (XIIIb) obtained as described in Example 15, were dissolved in 30 ml of 1,2-dichlorobenzene (Aldrich). The solution obtained was then uniformly deposited on a sheet of polymethyl methacrylate (dimensions 300 mm×90 mm×6 mm) using a film-forming device of the "Doctor Blade" type and the solvent was allowed to evaporate off at ambient temperature (25° C.), in a gentle flow of air, for 24 hours. From this there resulted a transparent sheet of orange color imparted by the film, the thickness of which was ranging from 100 µm to 50 µm.

An IXYS-KXOB22-12 photovoltaic cell having a surface area of 1.2 cm$^2$ was then applied to one of the edges of the polymer sheet.

The main surface of the polymer sheet (that coated with the thin film) was then illuminated with a light source of power 1 sun (1000 W/m$^2$) and the electrical power generated through the effect of the illumination was measured.

The power (P) measurements have been realized by illuminating a portion of sheet of dimensions 100 mm×90 mm, at an increasing distance (d) from the edge to which the photovoltaic cell was attached. These measurements at a variable distance from the photovoltaic cell allow the quantification of the contribution of wave guide, edge and autoabsorption effects.

It will be seen that, in the absence of edge effects, the mean power generated was 6.99 mW (FIG. 1).

EXAMPLE 20

6 g of Altuglas VSUVT 100 polymethyl methacrylate (PMMA) and 135.2 mg of methyl 4-{4,7-bis[5-(2,6-dimethylphenyl)(2-thienyl)]-6-phenoxy benzo [3,4-c]1,2,5-thiadiazo-5-yloxy}benzoate having formula (IId) obtained as described in Example 5, were dissolved in 30 ml of 1,2-dichlorobenzene (Aldrich). The solution obtained was then uniformly deposited on a sheet of polymethyl methacrylate (dimensions 300 mm×90 mm×6 mm) using a film-forming device of the "Doctor Blade" type and the solvent was allowed to evaporate off at ambient temperature (25° C.), in a gentle flow of air, for 24 hours. From this there resulted a transparent sheet of orange color imparted by the film, the thickness of which was ranging from 100 µm to 50 µm.

An IXYS-KXOB22-12 photovoltaic cell having a surface area of 1.2 cm$^2$ was then applied to one of the edges of the polymer sheet.

The main surface of the polymer sheet (that coated with the thin film) was then illuminated with a light source of power 1 sun (1000 W/m$^2$) and the electrical power generated through the effect of the illumination was measured The power (P) measurements have been realized by illuminating a portion of sheet of dimensions 100 mm×90 mm, at an increasing distance (d) from the edge to which the photovoltaic cell was attached. These measurements at a variable distance from the photovoltaic cell allow the quantification of the contribution of wave guide, edge and autoabsorption effects.

It will be seen that, in the absence of edge effects, the mean power generated was 12.19 mW (FIG. 1).

EXAMPLE 21

6 g of Altuglas VSUVT 100 polymethyl methacrylate (PMMA) and 145.6 mg of 4-{4,7-bis[5-(2,6-dimethylphenyl)(2-thienyl)]-6-[4-(methoxy carbonyl) phenoxy]benzo-[3,4-c]1,2,5-thiadiazo-5-yloxy} benzoate having formula (IIe) obtained as described in Example 7, were dissolved in 30 ml of 1,2-dichlorobenzene (Aldrich). The solution obtained was then uniformly deposited on a sheet of polymethyl methacrylate (dimensions 300 mm×90 mm×6 mm) using a film-forming device of the "Doctor Blade" type and the solvent was allowed to evaporate off at ambient temperature (25° C.), in a gentle flow of air, for 24 hours. From this there resulted a transparent sheet of orange color imparted by the film, the thickness of which was ranging from 100 μm to 50 μm. An IXYS-KXOB22-12 photovoltaic cell having a surface area of 1.2 cm² was then applied to one of the edges of the polymer sheet.

The main surface of the polymer sheet (that coated with the thin film) was then illuminated with a light source of power 1 sun (1000 W/m²) and the electrical power generated through the effect of the illumination was measured The power (P) measurements have been realized by illuminating a portion of sheet of dimensions 100 mm×90 mm, at an increasing distance (d) from the edge to which the photovoltaic cell was attached. These measurements at a variable distance from the photovoltaic cell allow the quantification of the contribution of wave guide, edge and autoabsorption effects.

It will be seen that, in the absence of edge effects, the mean power generated was 11.23 mW (FIG. 1).

EXAMPLE 22

6 g of Altuglas VSUVT 100 polymethyl methacrylate (PMMA) and 115.3 mg of 2-[4-(6-phenoxy-4,7-di(2-thienyl)benzo[3,4-c]1,2,5-thiadiazo-5-yloxy) phenylcarbonyloxy]ethyl 2-methylprop-2-enoate having formula (Ia) obtained as described in Example 9, were dissolved in 30 ml of 1,2-dichlorobenzene (Aldrich). The solution obtained was then uniformly deposited on a sheet of polymethyl methacrylate (dimensions 300 mm×90 mm×6 mm) using a film-forming device of the "Doctor Blade" type and the solvent was allowed to evaporate off at ambient temperature (25° C.), in a gentle flow of air, for 24 hours. From this there resulted a transparent sheet of orange color imparted by the film, the thickness of which was ranging from 100 μm to 50 μm.

An IXYS-KXOB22-12 photovoltaic cell having a surface area of 1.2 cm² was then applied to one of the edges of the polymer sheet.

The main surface of the polymer sheet (that coated with the thin film) was then illuminated with a light source of power 1 sun (1000 W/m²) and the electrical power generated through the effect of the illumination was measured The power (P) measurements have been realized by illuminating a portion of sheet of dimensions 100 mm×90 mm, at an increasing distance (d) from the edge to which the photovoltaic cell was attached. These measurements at a variable distance from the photovoltaic cell allow the quantification of the contribution of wave guide, edge and autoabsorption effects.

It will be seen that, in the absence of edge effects, the mean power generated was 8.29 mW (FIG. 1).

EXAMPLE 23

6 g of Altuglas VSUVT 100 polymethyl methacrylate (PMMA) and 143.4 mg of 2-{4-[6-(4-{[2-(2-methylprop-2-enoyloxy)ethyl]oxycarbonyl} phenoxy)-4,7-di(2-thienyl)benzo[3,4-c]1,2,5-thiadiazo-5-yloxy]phenylcarbonyl oxy}ethyl 2-methylprop-2-enoate having formula (Ib) obtained as described in Example 11, were dissolved in 30 ml of 1,2-dichlorobenzene (Aldrich). The solution obtained was then uniformly deposited on a sheet of polymethyl methacrylate (dimensions 300 mm×90 mm×6 mm) using a film-forming device of the "Doctor Blade" type and the solvent was allowed to evaporate off at ambient temperature (25° C.), in a gentle flow of air, for 24 hours. From this there resulted a transparent sheet of orange color imparted by the film, the thickness of which was ranging from 100 μm to 50 μm.

An IXYS-KXOB22-12 photovoltaic cell having a surface area of 1.2 cm² was then applied to one of the edges of the polymer sheet.

The main surface of the polymer sheet (that coated with the thin film) was then illuminated with a light source of power 1 sun (1000 W/m²) and the electrical power generated through the effect of the illumination was measured.

The power (P) measurements have been realized by illuminating a portion of sheet of dimensions 100 mm×90 mm, at an increasing distance (d) from the edge to which the photovoltaic cell was attached. These measurements at a variable distance from the photovoltaic cell allow the quantification of the contribution of wave guide, edge and autoabsorption effects.

It will be seen that, in the absence of edge effects, the mean power generated was 9.13 mW (FIG. 1).

EXAMPLE 24

6 g of Altuglas VSUVT 100 polymethyl methacrylate (PMMA) and 152.8 g of 2-(4-{4,7-bis[5-(2,5-dimethylphenyl)(2-thienyl)]-6-phenoxybenzo [3,4-c]1,2,5-thiadiazo-5-yloxy}phenylcarbonyloxy)ethyl-2-methylprop-2-enoate having formula (Ic) obtained as described in Example 13, were dissolved in 30 ml of 1,2-dichlorobenzene (Aldrich). The solution obtained was then uniformly deposited on a sheet of polymethyl methacrylate (dimensions 300 mm×90 mm×6 mm) using a film-forming device of the "Doctor Blade" type and the solvent was allowed to evaporate off at ambient temperature (25° C.), in a gentle flow of air, for 24 hours. From this there resulted a transparent sheet of orange color imparted by the film, the thickness of which was ranging from 100 μm to 50 μm.

An IXYS-KXOB22-12 photovoltaic cell having a surface area of 1.2 cm² was then applied to one of the edges of the polymer sheet.

The main surface of the polymer sheet (that coated with the thin film) was then illuminated with a light source of power 1 sun (1000 W/m) and the electrical power generated through the effect of the illumination was measured The power (P) measurements have been realized by illuminating a portion of sheet of dimensions 100 mm×90 mm, at an increasing distance (d) from the edge to which the photovoltaic cell was attached. These measurements at a variable distance from the photovoltaic cell allow the quantification of the contribution of wave guide, edge and autoabsorption effects.

It will be seen that, in the absence of edge effects, the mean power generated was 14.67 mW (FIG. 1).

The invention claimed is:

1. A disubstituted diaryloxybenzoheterodiazole compound having general formula (I) or (II):

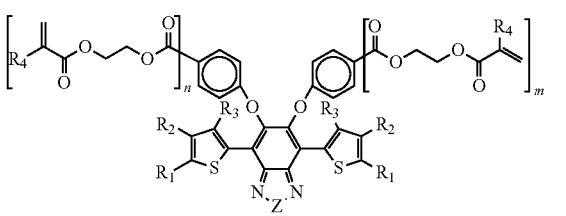

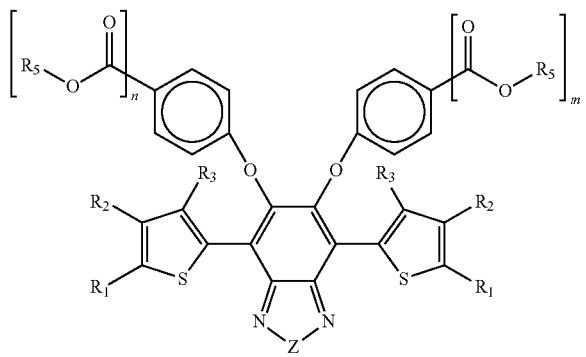

(II)

wherein:
- Z represents a sulfur atom, an oxygen atom, a selenium atom; or a group $NR_6$ wherein $R_6$ is selected from linear or branched $C_1$-$C_{20}$ alkyl groups, or from optionally substituted aryl groups;
- $R_1$, $R_2$ and $R_3$, identical or different, represent a hydrogen atom; or are selected from linear or branched $C_1$-$C_{20}$ alkyl groups optionally containing heteroatoms, optionally substituted cycloalkyl groups, optionally substituted aryl groups, optionally substituted, linear or branched $C_1$-$C_{20}$ alkoxy groups, optionally substituted phenoxy groups, or a cyano group;
- or $R_1$ and $R_2$, may optionally be bound together so as to form, together with carbon atoms to which $R_1$ and $R_2$ are bound, a saturated, unsaturated, or aromatic, cycle or a polycyclic system containing from 3 to 14 carbon atoms, optionally containing one or more heteroatoms including oxygen, sulfur, nitrogen, silicon, phosphorus, or selenium;
- or $R_2$ and $R_3$ may optionally be bound together so as to form, together with carbon atoms to which $R_2$ and $R_3$ are bound, a saturated, unsaturated, or aromatic, cycle or a polycyclic system containing from 3 to 14 carbon atoms, saturated, unsaturated, or aromatic, optionally containing one or more heteroatoms including oxygen, sulfur, nitrogen, silicon, phosphorus, or selenium;
- $R_4$, identical or different, represent hydrogen atoms; or are selected from linear or branched $C_1$-$C_{20}$ alkyl groups;
- $R_5$, identical or different, are selected from linear or branched $C_1$-$C_{20}$ alkyl groups optionally containing heteroatoms, or optionally substituted cycloalkyl groups;
- n and m, identical or different, are 0 or 1, provided that at least one of m and n is 1.

2. A disubstituted diaryloxybenzoheterodiazole compound according to claim 1, wherein in said general formula (I) or (II):
- Z represents a sulfur atom;
- $R_1$, mutually identical, represent hydrogen atoms or are selected from optionally substituted aryl groups;
- $R_2$ and $R_3$, mutually identical, represent a hydrogen atom;
- $R_4$, mutually identical, are selected from linear or branched $C_1$-$C_8$ alkyl groups;
- $R_5$, mutually identical, are selected from linear or branched $C_1$-$C_8$ alkyl groups;
- n and m, identical or different, are 0 or 1, provided that at least one of n and m is 1.

3. A process for the preparation of a disubstituted diaryloxybenzoheterodiazole compound having general formula (I):

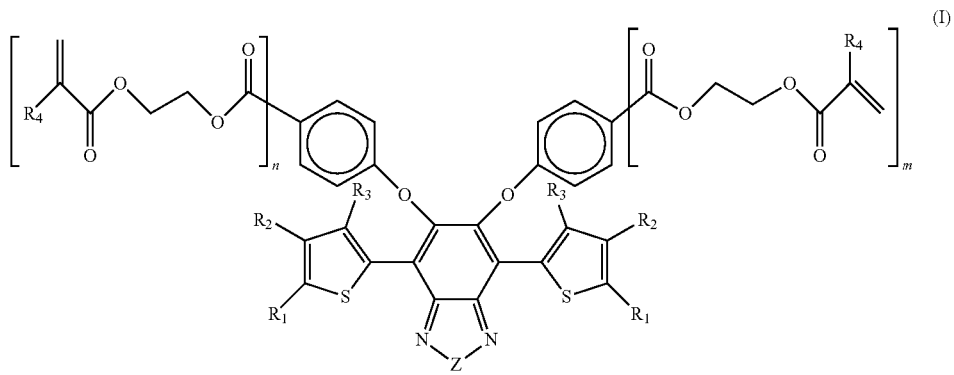

(I)

wherein:
- Z represents a sulfur atom, an oxygen atom, a selenium atom; or a group $NR_6$ wherein $R_6$ is selected from linear or branched $C_1$-$C_{20}$ alkyl groups, or from optionally substituted aryl groups;
- $R_1$, $R_2$ and $R_3$, identical or different, represent a hydrogen atom; or are selected from linear or branched $C_1$-$C_{20}$ alkyl groups optionally containing heteroatoms, optionally substituted cycloalkyl groups, optionally substituted aryl groups, optionally substituted, linear or branched $C_1$-$C_{20}$ alkoxy groups, optionally substituted phenoxy groups, or a cyano group;
- or $R_1$ and $R_2$, may optionally be bound together so as to form, together with carbon atoms to which $R_1$ and $R_2$ are bound, a saturated, unsaturated, or aromatic, cycle or a polycyclic system containing from 3 to 14 carbon atoms, optionally containing one or more heteroatoms including oxygen, sulfur, nitrogen, silicon, phosphorus, or selenium;
- or $R_2$ and $R_3$ may optionally be bound together so as to form, together with carbon atoms to which $R_2$ and $R_3$ are bound, a saturated, unsaturated, or aromatic, cycle or a polycyclic system containing from 3 to 14 carbon atoms, saturated, unsaturated, or aromatic, optionally containing one or more heteroatoms including oxygen, sulfur, nitrogen, silicon, phosphorus, or selenium;

$R_4$, identical or different, represent a hydrogen atom; or are selected from linear or branched $C_1$-$C_{20}$ alkyl groups;

n and m, identical or different, are 0 or 1, provided that at least one of m and n is 1;

comprising reacting at least one acid of a disubstituted diaryloxybenzoheterodiazole compound having general formula (III):

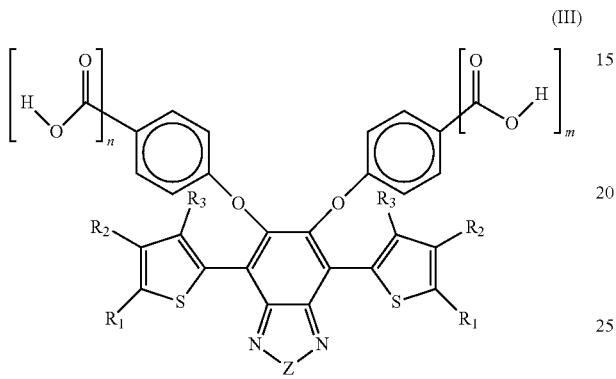

(III)

wherein Z, $R_1$, $R_2$, $R_3$, m and n have the same meanings described above, to react with at least one hydroxyalkyl (meth)acrylate in the presence of at least one carbodiimide and of at least one dialkylamino-pyridine, wherein:

said hydroxyalkyl (meth)acrylate is selected from: 2-hydroxyethyl acrylate, 2-hydroxyethyl methacrylate (HEMA), 2-hydroxypropyl acrylate, 2-hydroxypropyl methacrylate, 3-hydroxypropyl acrylate, 3-hydroxypropyl methacrylate, 3-hydroxybutyl acrylate, 3-hydroxybutyl methacrylate, 4-hydroxybutyl acrylate, 4-hydroxybutyl methacrylate, 6-hydroxyhexyl acrylate, 6-hydroxyhexyl methacrylate, 3-hydroxy-2-ethylhexyl acrylate, 3-hydroxy-2-ethylhexyl methacrylate, neopentyl glycol monoacrylate, neopentyl glycol monomethacrylate, 1,5-pentanediol monoacrylate, 1,5-pentanediol monomethacrylate, 1,6-hexanediol monoacrylate, 1,6-hexanediol monomethacrylate, or mixtures thereof; or said acid of a disubstituted diaryloxybenzoheterodiazole compound having general formula (III) and said hydroxyalkyl (meth)acrylate are used in molar ratios ranging from 1:3 to 1:15; or said carbodiimide is selected from: dicyclohexylcarbodiimide (DCC) or diisopropylcarbodiimide; or is 1-ethyl-[3-(3-dimethylamino)propyl]-carbodiimide hydrochloride (WSC); or said acid of a disubstituted diaryloxybenzoheterodiazole compound having general formula (III) and said carbodiimide are used in molar ratios ranging from 1:1 to 1:5; or said dialkyl-aminopyridine is selected from: N,N-dimethyl-4-aminopyridine (DMPA), N,N-diethyl-4-aminopyridine r N,N-dibutyl-4-aminopyridine; or said acid of a disubstituted diaryloxybenzoheterodiazole compound having general formula (III) and said dialkyl-aminopyridine are used in molar ratios ranging from 1:0.1 to 1:2; or said process is carried out in the presence of at least one organic solvent selected from: ethers selected from 1,2-dimethoxyethane, 1,4-dioxane, tetrahydrofuran, or mixtures thereof; hydrocarbons selected from toluene, xylene, or mixtures thereof; ester solvents selected from methyl acetate, ethyl acetate, or mixtures thereof; dipolar aprotic solvents selected from N,N-dimethylformamide, N-methylpyrrolidone, dimethyl sulfoxide, or mixtures thereof; chlorinated solvents selected from dichloromethane, dichloroethane, dichlorobenzene, or mixtures thereof; or mixtures thereof; or said acid of a disubstituted diaryloxybenzoheterodiazole compound having general formula (III) is used in said organic solvent in such a quantity as to have a molar concentration in said organic solvent ranging from 0.005 M to 2M;

said process is carried out at a temperature ranging from −40° C. to 40° C.; or said process is carried out for a time ranging from 1 hour to 30 hours.

4. A process for the preparation of a disubstituted diaryloxybenzoheterodiazole compound having general formula (II):

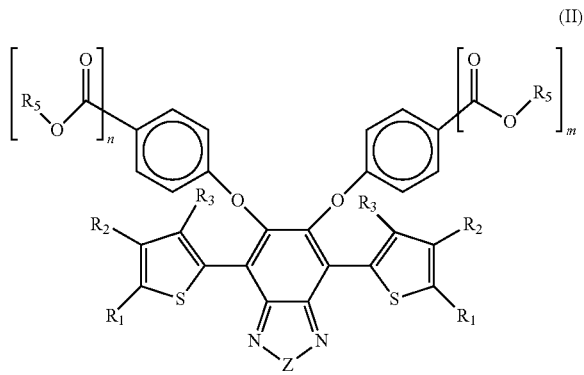

(II)

wherein:

Z represents a sulfur atom, an oxygen atom, a selenium atom; or a group $NR_6$ wherein $R_6$ is selected from linear or branched $C_1$-$C_{20}$ alkyl groups, or from optionally substituted aryl groups;

$R_2$ and $R_3$, identical or different, represent a hydrogen atom and provided that $R_1$ does not represent a hydrogen atom; or $R_1$, $R_2$ and $R_3$ are selected from linear or branched $C_1$-$C_{20}$ alkyl groups optionally containing heteroatoms, optionally substituted cycloalkyl groups, optionally substituted aryl groups, optionally substituted, linear or branched $C_1$-$C_{20}$ alkoxy groups, optionally substituted phenoxy groups, or a cyano group;

or $R_1$ and $R_2$, may optionally be bound together so as to form, together with carbon atoms to which $R_1$ and $R_2$ are bound, a saturated, unsaturated, or aromatic, cycle or a polycyclic system containing from 3 to 14 carbon atoms, optionally containing one or more heteroatoms selected from oxygen, sulfur, nitrogen, silicon, phosphorus, or selenium;

or $R_2$ and $R_3$ may optionally be bound together so as to form, together with carbon atoms to which $R_2$ and $R_3$ are bound, a saturated, unsaturated, or aromatic, cycle or a polycyclic system containing from 3 to 14 carbon atoms, saturated, unsaturated, or aromatic, optionally containing one or more heteroatoms selected from oxygen, sulfur, nitrogen, silicon, phosphorus, or selenium;

$R_5$, identical or different, are selected from linear or branched $C_1$-$C_{20}$ alkyl groups optionally containing heteroatoms, or optionally substituted cycloalkyl groups;

and n and m are equal to 1, comprising:

(a) causing at least one disubstituted fluorinated benzoheterodiazole compound having general formula (IV):

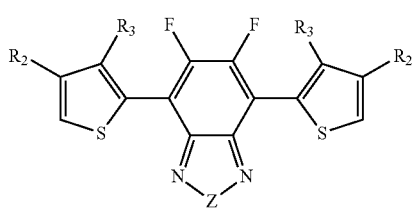

(IV)

wherein Z, $R_2$ and $R_3$ have the same meanings described above, to react with at least one alkyl 4-hydroxybenzoate having general formula (V):

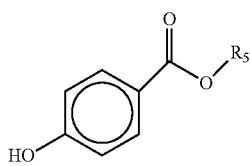

(V)

wherein $R_5$ has the same meanings described above, obtaining a disubstituted diaryloxybenzoheterodiazole compound having general formula (VI):

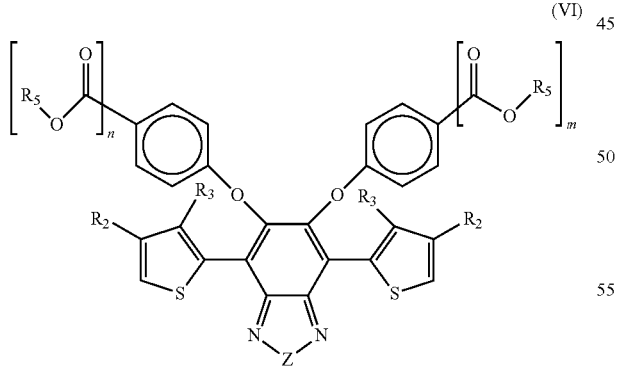

(VI)

wherein Z, $R_2$, $R_3$ and $R_5$, have the same meanings described above, and n and m are equal to 1;

(b) causing at least one disubstituted diaryloxybenzoheterodiazole compound having general formula (VI) obtained in step (a) to react with at least one compound selected from N-haloimides selected from N-bromosuccinimide, N-bromophthalimide, N-iodosuccinimide, and N-iodophthalimide, obtaining a disubstituted halogenated diaryloxybenzoheterodiazole compound having general formula (VII):

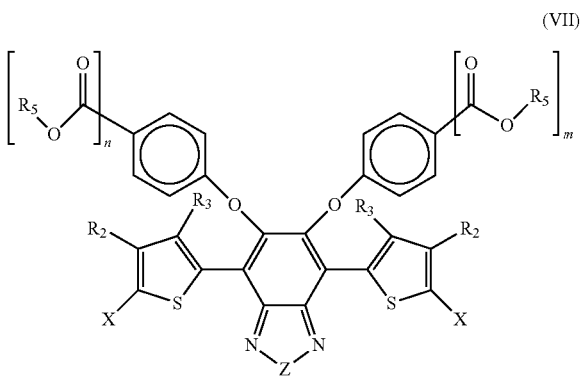

(VII)

wherein Z, $R_2$, $R_3$ and $R_5$, have the same meanings described above, and X is a halogen atom selected from bromine or iodine; and (c) causing at least one disubstituted halogenated diaryloxybenzoheterodiazole compound having general formula (VII) obtained in step (b) to react with at least one aryl-boron compound having general formula (VIII):

(VIII)

wherein $R_1$ has the same meanings described above and the $R_7$ substituents represent a hydrogen atom, or are selected from linear or branched $C_1$-$C_{10}$ alkyl groups, or from optionally substituted cycloalkyl groups, or the two $R_7$ substituents may optionally be bound together so as to form, together with the other atoms to which the two $R_7$ substituents are bound, a cyclic compound;

optionally, in said step (a) said disubstituted fluorinated diaryloxybenzoheterodiazole compound having general formula (IV) and said alkyl 4-hydroxybenzoate having general formula (V) are used in molar ratios ranging from 1:2 to 1:10; or said step (a) is carried out in the presence of at least one weak organic base selected from: alkali metal or alkaline-earth metal carboxylates, selected from potassium acetate, sodium acetate, cesium acetate, magnesium acetate, calcium acetate, propionate potassium, sodium propionate, cesium propionate, magnesium propionate, calcium propionate, or mixtures thereof; alkali metal or alkaline-earth metal carbonates, selected from lithium carbonate, potassium carbonate, sodium carbonate, cesium carbonate, magnesium carbonate, calcium carbonate, or mixtures thereof; alkali metal or alkaline-earth metal bicarbonates selected from lithium bicarbonate, potassium bicarbonate, sodium bicarbonate, cesium bicarbonate, magnesium bicarbonate, calcium bicarbonate, or mixtures thereof; or mixtures thereof; or said disubstituted fluorinated diaryloxybenzoheterodiazole compound having general formula (IV) and said weak organic base are used in molar ratios ranging from 1:1 to 1:10; or said step (a) is carried out in the presence of at least one organic solvent selected from: ethers selected from 1,2-dimethoxyethane, 1,4-dioxane, tetrahydrofuran, or mixtures thereof; chlorinated solvents selected from dichloromethane, chloroform, or mixtures thereof; dipolar aprotic solvents selected from N,N-dimethylformamide, N-methylpyrrolidone, dimethyl sulfoxide; or mixtures thereof; or said disubstituted fluorinated diaryloxybenzoheterodiazole compound having general formula (IV) is used in said organic solvent in such a quantity as to have a molar concentration in said organic solvent ranging from 0.05 M to 2 M; or said step (a) is carried out at a temperature ranging from 60° C. to 150° C.; or said step (a) is carried out for a time ranging from 1 hour to 24 hours; or in said step (b) said disubstituted diaryloxybenzoheterodiazole compound having general formula (VI) and said compound selected from N-haloimides are used in molar ratios ranging from 1:2 to 1:3; or said step (b) is carried out in the presence of at least one organic solvent selected from: ethers selected from 1,2-dimethoxyethane, 1,4-dioxane, and tetrahydrofuran, or mixtures thereof; chlorinated solvents selected from dichloromethane, and chloroform, or mixtures thereof; dipolar aprotic solvents selected from N,N-dimethylformamide, N-methylpyrrolidone, and dimethyl sulfoxide; or mixtures thereof; or said disubstituted diaryloxybenzoheterodiazole compound having general formula (VI) is used in said organic solvent in such a quantity as to have a molar concentration in said organic solvent ranging from 0.01 M to 5 M; or said step (b) is carried out at a temperature ranging from 20° C. to 50° C.; or said step (b) is carried out for a time ranging from 1 hour to 24 hours; or in said step (c) said disubstituted halogenated diaryloxybenzoheterodiazole compound having general formula (VII) and said aryl-boron compound having general formula (VIII), are used in molar ratios ranging from 1:2 to 1:5; or said step (c) is carried out in the presence of at least one palladium-containing catalyst selected from compounds of palladium in the oxidation state (0) or (II) selected from palladium-tetrakistriphenylphosphine [Pd(PPh$_3$)$_4$] or bis-triphenylphosphine palladium dichloride [PdCl$_2$(PPh$_3$)$_2$]; or said disubstituted halogenated diaryloxybenzoheterodiazole compound having general formula (VII) and said catalyst are used in molar ratios ranging from 1:0.15 to 1:0.01; or said step (c) is carried out in the presence of at least one weak organic base selected from: alkali metal or alkaline-earth metal carboxylates selected from potassium acetate, sodium acetate, cesium acetate, magnesium acetate, calcium acetate, propionate potassium, sodium propionate, cesium propionate, magnesium propionate, calcium propionate, or mixtures thereof; alkali metal or alkaline-earth metal carbonates selected from lithium carbonate, potassium carbonate, sodium carbonate, cesium carbonate, magnesium carbonate, calcium carbonate, or mixtures thereof; alkali metal or alkaline-earth metal bicarbonates selected from lithium bicarbonate, potassium bicarbonate, sodium bicarbonate, cesium bicarbonate, magnesium bicarbonate, calcium bicarbonate, or mixtures thereof; or mixtures thereof; or said disubstituted halogenated diaryloxybenzoheterodiazole compound having general formula (VII) and said weak organic base are used in molar ratios ranging from 1:1 to 1:20; or said step (c) is carried out in the presence of at least one organic solvent selected from: ethers selected from 1,2-dimethoxyethane, 1,4-dioxane, tetrahydrofuran, or mixtures thereof; hydrocarbons selected from toluene, xylene, or mixtures thereof; dipolar aprotic solvents selected from N,N-dimethylformamide, N-methylpyrrolidone, dimethyl sulfoxide, or mixtures thereof; or mixtures thereof; or in said step (b), said organic solvent may be used in mixture with at least one alcohol selected from methanol, ethanol, n-propanol, iso-propanol, or mixtures thereof; or said disubstituted halogenated diaryloxybenzoheterodiazole compound having general formula (VII) is used in said organic solvent in such a quantity as to have a molar concentration in said organic solvent ranging from 0.01 M to 2 M; or said step (c) is carried out at a temperature ranging from 50° C. to 140° C.; or said step (c) is carried out for a time ranging from 2 hours to 36 hours.

5. A process for the preparation of a disubstituted diaryloxybenzoheterodiazole compound having general formula (II):

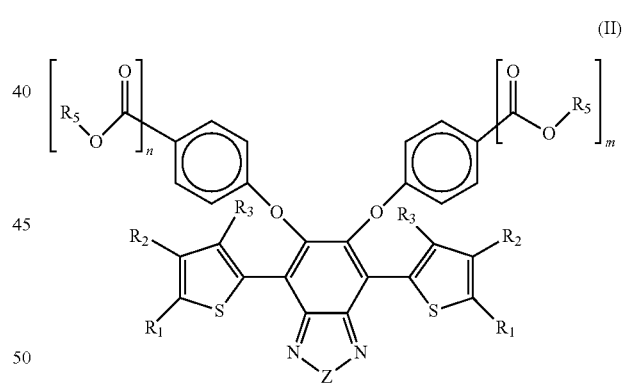

wherein:

Z represents a sulfur atom, an oxygen atom, a selenium atom; or a group NRG wherein $R_6$ is selected from linear or branched $C_1$-$C_{20}$ alkyl groups, or from optionally substituted aryl groups;

$R_2$ and $R_3$, identical or different, represent a hydrogen atom, provided that $R_1$ does not represent a hydrogen atom, or $R_1$, $R_2$ and $R_3$ are selected from linear or branched $C_1$-$C_{20}$ alkyl groups optionally containing heteroatoms, optionally substituted cycloalkyl groups, optionally substituted aryl groups, optionally substituted, linear or branched $C_1$-$C_{20}$ alkoxy groups, optionally substituted phenoxy groups, or a cyano group;

or $R_1$ and $R_2$, may optionally be bound together so as to form, together with carbon atoms to which $R_1$ and $R_2$ are bound, a saturated, unsaturated, or aromatic, cycle or a polycyclic system containing from 3 to 14 carbon atoms, optionally containing one or more heteroatoms including oxygen, sulfur, nitrogen, silicon, phosphorus, or selenium;

or $R_2$ and $R_3$ may optionally be bound together so as to form, together with carbon atoms to which $R_2$ and $R_3$ are bound, a saturated, unsaturated, or aromatic, cycle or a polycyclic system containing from 3 to 14 carbon atoms, saturated, unsaturated, or aromatic, optionally containing one or more heteroatoms including oxygen, sulfur, nitrogen, silicon, phosphorus, or selenium;

$R_5$, identical or different, are selected from linear or branched $C_1$-$C_{20}$ alkyl groups optionally containing heteroatoms, or optionally substituted cycloalkyl groups;

and if n is 0, m is 1 or vice versa, comprising:

($a_1$) causing at least one disubstituted fluorinated diaryloxybenzoheterodiazole compound having general formula (IV):

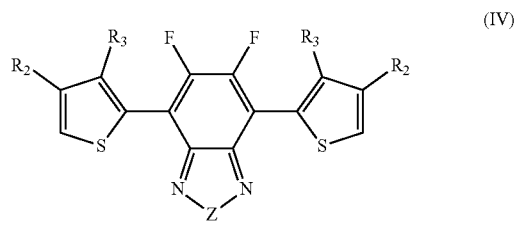

(IV)

wherein Z, $R_2$ and $R_3$ have the same meanings described above, to react with at least one alkyl 4-hydroxybenzoate having general formula (V):

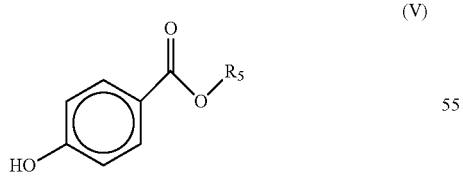

(V)

wherein $R_5$ has the same meanings described above, said disubstituted fluorinated diaryloxybenzoheterodiazole compound having general formula (IV) and said alkyl 4-hydroxybenzoate having general formula (V) being used in equal molar ratios, obtaining a reaction mixture comprising at least one disubstituted fluorinated monoaryloxybenzoheterodiazole compound having general formula (VIa):

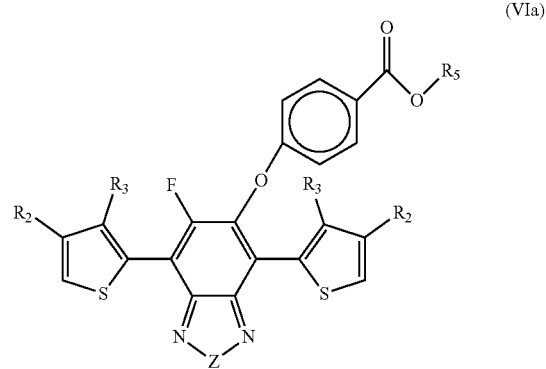

(VIa)

wherein Z, $R_2$, $R_3$ and $R_5$, have the same meanings described above, and m is 1;

($b_1$) adding directly to the reaction mixture obtained in step ($a_1$) at least one phenol having formula (IX), said phenol having formula (IX) being used in equal molar ratios or in molar excess with respect to said disubstituted fluorinated diaryloxybenzoheterodiazole compound having general formula (IV):

(IX)

obtaining a disubstituted diaryloxybenzoheterodiazole compound having general formula (X):

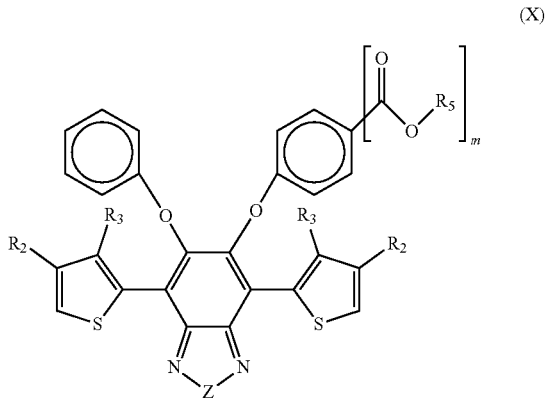

(X)

wherein Z, $R_2$, $R_3$ and $R_5$ have the same meanings described above and m is 1;

($c_1$) causing at least one disubstituted diaryloxybenzoheterodiazole compound having general formula (X) obtained in the step ($b_1$) to react with at least one compound selected from N-haloimides selected from N-bromosuccinimide, N-bromophthalimide, N-iodosuccinimide, or N-iodophthalimide, obtaining a disubstituted halogenated diaryloxybenzoheterodiazole compound having general formula (XI):

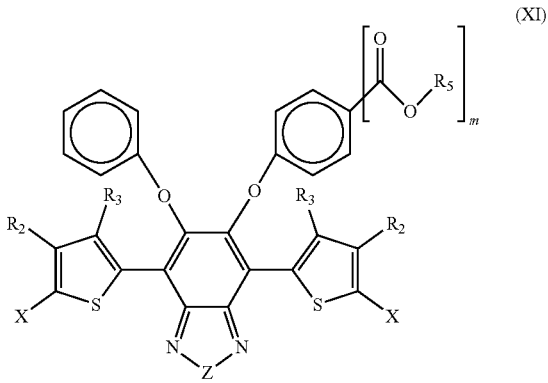

wherein Z, $R_2$, $R_3$ and $R_5$, have the same meanings described above, and X is a halogen atom selected from bromine or iodine;

($d_1$) causing at least one disubstituted halogenated diaryloxybenzoheterodiazole compound having general formula (XI) obtained in the step ($c_1$) to react with at least one aryl-boron compound having general formula (VIII):

wherein $R_1$ has the same meanings described above and the $R_7$ substituents represent a hydrogen atom or are selected from linear or branched $C_1$-$C_{10}$ alkyl groups, or from optionally substituted cycloalkyl groups, or the two $R_7$ substituents may optionally be bound together so as to form, together with other atoms to which the two $R_7$ substituents are bound, a cyclic compound;

optionally, said step ($a_1$) is carried out in the presence of at least one weak organic base selected from: alkali metal or alkaline-earth metal carboxylates selected from potassium acetate, sodium acetate, cesium acetate, magnesium acetate, calcium acetate, propionate potassium, sodium propionate, cesium propionate, magnesium propionate, calcium propionate, or mixtures thereof; alkali metal or alkaline-earth metal carbonates selected from lithium carbonate, potassium carbonate, sodium carbonate, cesium carbonate, magnesium carbonate, calcium carbonate, or mixtures thereof; alkali metal or alkaline-earth metal bicarbonates selected from lithium bicarbonate, potassium bicarbonate, sodium bicarbonate, cesium bicarbonate, magnesium bicarbonate, calcium bicarbonate, or mixtures thereof; or mixtures thereof; or said disubstituted fluorinated diaryloxybenzoheterodiazole compound having general formula (IV) and said weak organic base are used in molar ratios ranging from 1:1 to 1:10; or said step ($a_1$) is carried out in the presence of at least one organic solvent which is selected from: ethers selected from 1,2-dimethoxyethane, 1,4-dioxane, tetrahydrofuran, or mixtures thereof; chlorinated solvents selected from dichloromethane, chloroform, or mixtures thereof; dipolar aprotic solvents selected from N,N-dimethylformamide, N-methylpyrrolidone or dimethyl sulfoxide; or mixtures thereof; or said disubstituted fluorinated diaryloxybenzoheterodiazole compound having general formula (IV) is used in said organic solvent in such a quantity as to have a molar concentration in said organic solvent ranging from 0.05 M to 2 M; or said step ($a_1$), and said step ($b_1$), are carried out at a temperature ranging from 60° C. to 150° C.; or said step ($a_1$) and said step ($b_1$), independently, are carried out for a time ranging from 1 hour to 24 hours.

6. A luminescent solar concentrator (LSC) including at least one disubstituted diaryloxybenzoheterodiazole compound having general formula (I) or (II) according to claim 1.

7. A photovoltaic or solar device comprising at least one photovoltaic or solar cell, and at least one said luminescent solar concentrator (LSC) according to claim 6.

8. A method, comprising dispersing or chemically binding at least one disubstituted diaryloxybenzoheterodiazole compound having general formula (I) or (II) according to claim 1, in or to a material transparent to solar radiation in a luminescent solar concentrator (LSC).

* * * * *